United States Patent [19]
Bootz et al.

[11] Patent Number: 5,686,642
[45] Date of Patent: Nov. 11, 1997

[54] COMPOUNDS USEFUL FOR THE PREPARATION OF BI-AND POLYFUNCTIONAL REACTIVE DYESTUFFS

[75] Inventors: Konrad Bootz, Wetter; Manfred Hoppe; Eckhard Bock, both of Kürten-Bechen; Wolfram Reddig, Bergisch Gladbach; Thomas Eizenhöfer, Cologne; Wolfgang Harms, Odenthal; Karl-Josef Herd, Odenthal-Holz, all of Germany

[73] Assignee: Bayer Aktiengesellschaft, Leverkusen, Germany

[21] Appl. No.: 682,039

[22] Filed: Jul. 16, 1996

Related U.S. Application Data

[62] Division of Ser. No. 54,118, Apr. 27, 1993, Pat. No. 5,597,902.

[30] Foreign Application Priority Data

May 4, 1992 [DE] Germany .............. 42 14 743.3
Feb. 16, 1993 [DE] Germany .............. 43 04 614.2

[51] Int. Cl.$^6$ .............. C07C 315/02; C07C 317/28; C07C 319/14; C07C 323/25
[52] U.S. Cl. .............. 558/29; 558/169; 560/250; 560/252; 560/309; 562/58; 564/440
[58] Field of Search .............. 558/29, 169; 560/250, 560/252, 309; 562/58; 564/440

[56] References Cited

U.S. PATENT DOCUMENTS

| | | | |
|---|---|---|---|
| 3,380,991 | 4/1968 | Dale, III et al. | 564/440 X |
| 4,560,388 | 12/1985 | Rohrer | 534/638 X |
| 4,754,023 | 6/1988 | Tzikas et al. | 534/638 X |
| 4,845,203 | 7/1989 | Dietz et al. | 534/637 |
| 4,908,436 | 3/1990 | Scheibli | 534/637 |
| 4,979,961 | 12/1990 | Junino et al. | 564/440 X |
| 5,243,034 | 9/1993 | Tappe et al. | 534/637 |
| 5,405,947 | 4/1995 | Hoppe et al. | 558/29 X |
| 5,410,081 | 4/1995 | Kunde et al. | 564/440 X |

FOREIGN PATENT DOCUMENTS

| | | |
|---|---|---|
| 74928 | 3/1983 | European Pat. Off. . |
| 141367 | 5/1985 | European Pat. Off. . |
| 70806 | 5/1985 | European Pat. Off. . |
| 70807 | 5/1985 | European Pat. Off. . |
| 395951 | 11/1990 | European Pat. Off. . |
| 2346418 | 10/1977 | France . |
| 1576237 | 10/1980 | United Kingdom . |

OTHER PUBLICATIONS

D. Feldman et al., "Polymerization and . . . Derivatives," Buletinul Institututlui Politehnic Din Iasi, Jun. 11, 1970, pp. 213–220.
Chemical Abstracts, vol. 81, 1974, p. 36, 50515q.
Chemical Abstracts, Vo. 75, 1971, p. 31, 119130f.

*Primary Examiner*—Fiona T. Powers
*Attorney, Agent, or Firm*—Sprung Kramer Schaefer & Briscoe

[57] ABSTRACT

Reactive dyestuffs which, in the form of the free acid, correspond to the following formula $$D\left[W-N(R^1)-C(=N)-N=C(X)-N-N(-CH_2-CH_2-O)_n-(CH_2)_r-SO_2-Z)\right]_m \quad (I)$$

(with aromatic ring bearing $R^2$ and $(SO_3H)_j$)

wherein

D is the radical of an organic dyestuff of the mono-azo, polyazo or metal complex azo series and the other substituents have the meaning given in the description, show improved application properties.

2 Claims, No Drawings

COMPOUNDS USEFUL FOR THE PREPARATION OF BI-AND POLYFUNCTIONAL REACTIVE DYESTUFFS

This is a division of application Ser. No. 08/054,118, filed on Apr. 27, 1993 now U.S. Pat. No. 5,597,902.

The invention relates to new bi- and polyfunctional reactive dyestuffs, their preparation and their use.

Although bifunctional reactive dyestuffs are known, for example, from DE-A-2 614 550, EP-A-70 807, EP-A-70 806 and EP-A-74 928, and tri- and tetrafunctional reactive dyestuffs, for example, from EP-A-395 951, the known reactive dyestuffs still have various disadvantages in their application, for example too low a fixing yield.

The present invention relates to new reactive dyestuffs of the formula

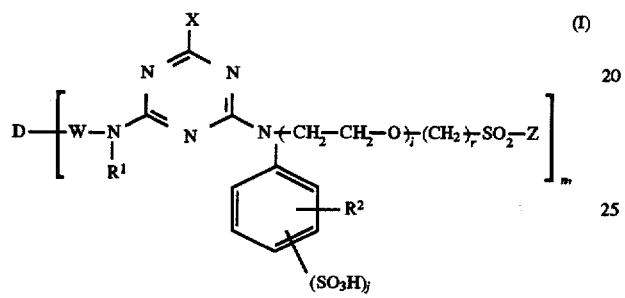

wherein

D denotes the radical of an organic dyestuff of the monoazo, polyazo or metal complex azo series, W denotes a direct bond or bridge member, $R^1$ denotes H or $C_1$–$C_4$-alkyl, which can be substituted by OR, $OSO_3H$, $SO_3H$, COOR or halogen, R denotes H, $CH_3$ or $C_2H_5$, $R^2$ denotes H, $C_1$–$C_4$-alkyl, Cl, Br, $C_1$–$C_4$-alkoxy or COOH, i denotes 0 or 1, j denotes 0, 1 or 2, r denotes 2 or 3, preferably 2, X denotes F, Cl or Br, Z denotes —CH=$CH_2$, —$CH_2$—$CH_2$—$OSO_3H$, —$CH_2$—$CH_2$—Cl, —$CH_2$—$CH_2$—Br, —$CH_2$—$CH_2$—$S_2O_3H$, —$CH_2$—$CH_2$—O—CO—$CH_3$, —$CH_2$—$CH_2$—$OPO_3H_2$ or —$CH_2$—$CH_2$—OH, and n denotes 1 or 2, with the exception of the compounds known from EP-A-70 806

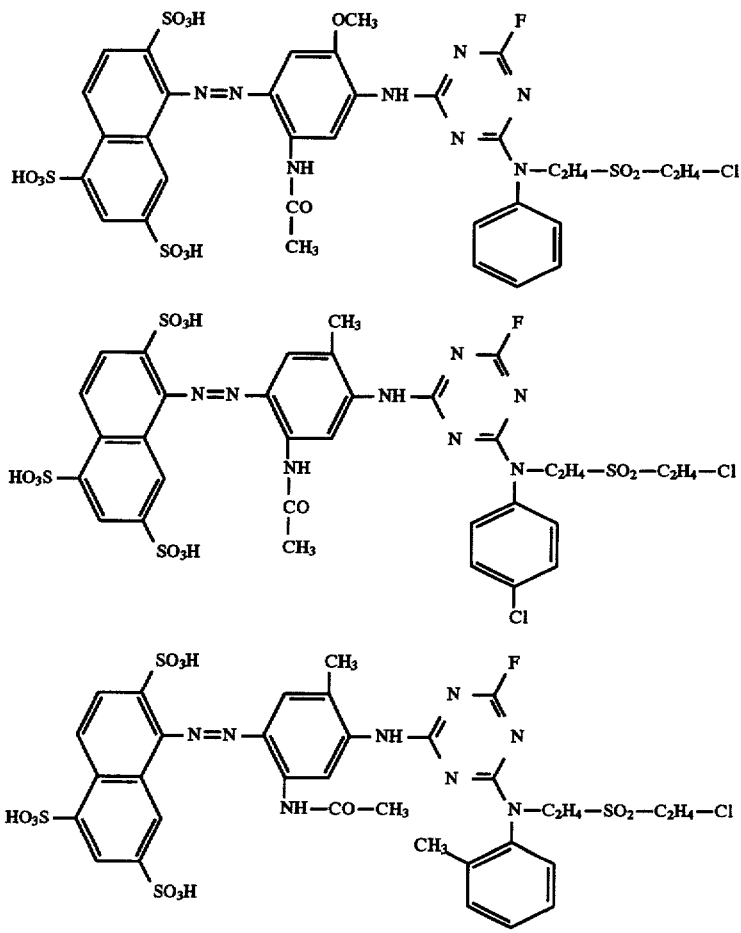

Particularly preferred radicals Z are —CH=CH$_2$ and —C$_2$H$_4$—OSO$_3$H.

The following applies to the alkyl, aryl, aralkyl, hetaryl, alkoxy, halogen and acylamino radicals mentioned in the present application and to the bridge members:

Alkyl groups are understood as meaning, in particular, those having 1 to 4 C atoms, which can optionally contain substituents, for example halogen, such as Cl or Br, CN, CO$_2$H, SO$_3$H or OSO$_3$H.

Alkoxy radicals are understood as meaning, in particular, those having 1 to 4 C atoms.

Halogen is understood as meaning, in particular, chlorine or fluorine.

Acylamino radicals are understood as meaning, in particular, those having 1 to 4 C atoms, such as formylamino, acetylamino, propionylamino or n-butyrylamino.

Suitable bridge members W are, for example:

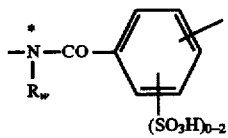

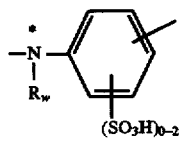

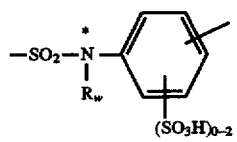

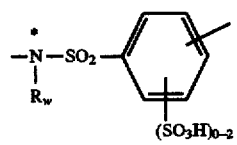

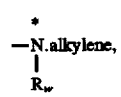

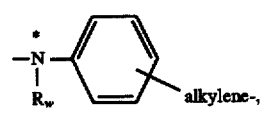

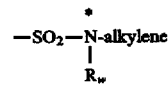

wherein R$_w$ represents hydrogen or alkyl, and alkylene denotes an alkylene radical having 1 to 6 C atoms, * identifying the atom or group bonded to the chromophore D.

Alkylene radicals which may be mentioned are: —CH$_2$—, —CH$_2$—CH$_2$—,

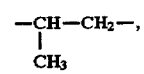

—(CH$_2$)$_3$—, —(CH$_2$)$_4$— or —(CH$_2$)$_6$—.

The present invention furthermore relates to the preparation of the reactive dyestuffs of the formula (I) by methods which are known per se:

a) either by condensation of dyestuffs of the formula

wherein
D, W, R$^1$ and n have the abovementioned meaning, with n mol of trihalogenotriazines of the formula

to give compounds of the formula

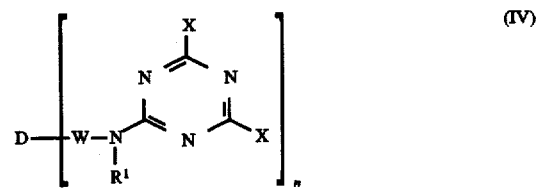

and further condensation of the compounds of the formula (IV) with n mol of components of the formula

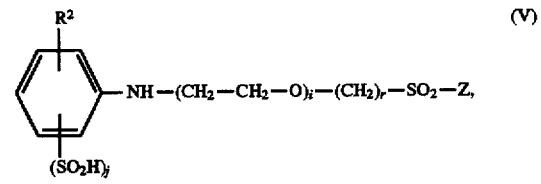

wherein
R$^2$, i, j, r, X and Z have the abovementioned meaning, or b) in reverse sequence, by condensation of trihalogenotriazines of the formula (III) with components of the formula (V) to give the primary condensation products

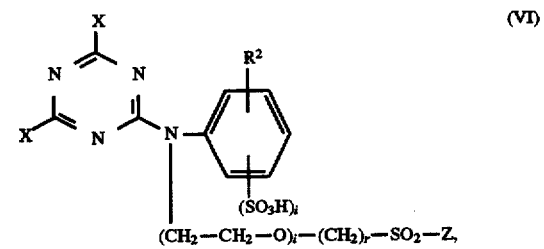

wherein
X, i, R$^2$, j, r and Z have the abovementioned meaning, and further condensation with n mol of the compounds of the formula (VI) with the dyestuffs of the formula (II), or c) by condensation of suitable precursors with the trihalogenotriazines (III) and components of the formula (V), or by condensation of suitable precursors with the primary condensation products of the formula (VI) and subsequent dyestuff synthesis.

The invention furthermore relates to a process for the preparation of compounds (V) and intermediate products (V) and intermediate products useful for their preparation of the general formula

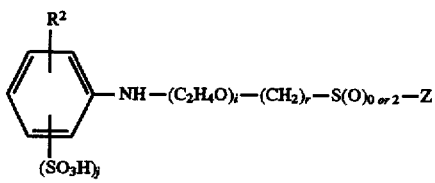

including their salts and their reaction products with protective groups, wherein $R^2$, Z, j, i and r have the meaning given under formula (I), with the exception of the compound

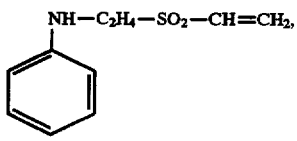

which is described as a monomer in an acrylonitrile/vinyl sulphone copolymer by D. Feldman and I. Negulescu in Bul. Inst. Politeh. Iasi 16 (1970) 213–220 (CA 75: 119130f) and by I. Negulescu in RO 59 096 of 15th Nov. 1973 (CA 81: 50515q).

Particularly preferred compounds are those wherein $R^2$ denotes H, j and i denote 0 and r denotes 2.

The compounds of the formula (V) can be prepared by sulphation of compounds of the formula

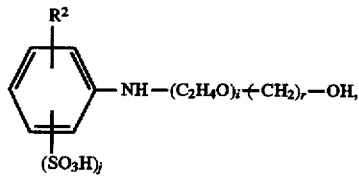

subsequent reaction with mercaptoethanol to give

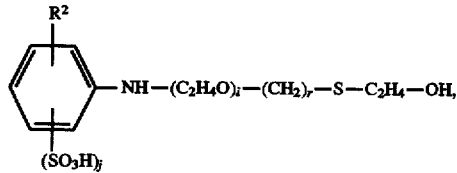

if appropriate blocking of the NH group with a protective group, in particular acetyl, and oxidation, in particular with $H_2O_2$, to give

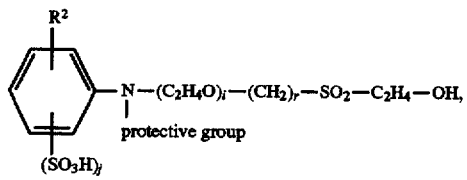

if appropriate splitting off of the protective group to give

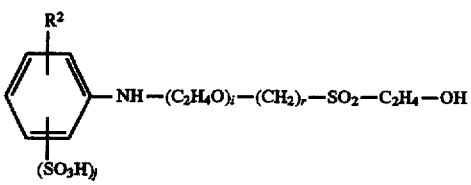

and if appropriate customary conversion of the radical $SO_2C_2H_4$—OH into the vinylsulphonyl group or conversion of the —$CH_2$—$CH_2$—OH group into the other detachable groups listed under Z.

The condensations of the starting components with the trihalogenotriazines are carried out in aqueous or organic-aqueous media in the presence of acid-binding agents, regardless of the sequence. Depending on the nature of the starting components, the first stage of the condensation here is carried out in pH ranges from 2 to 8, preferably 3 to 7, and at temperatures of 0° to 40° C., preferably 0° to 25° C. The replacement of the second halogen atom of the triazine takes place in the pH range from 4 to 10, preferably 5 to 9, and in the temperature range from 0° to 60° C., preferably 0° to 30° C.

Acid-binding agents are, for example, carbonates, hydroxides or phosphates, such as sodium carbonate, sodium bicarbonate, dilute sodium hydroxide solution, di- or trisodium phosphate or sodium fluoride.

If the condensation or the dyestuff synthesis is to lead directly to a dyestuff solution or to a liquid dyestuff preparation, it may be advantageous to use lithium carbonates or lithium hydroxide, if appropriate together with solubilising agents and/or stabilising buffer systems. Other conversion reactions of the dyestuffs or precursors thereof, such as metallisation reactions, sulphonations or introduction of acylamino groupings, can in general be carried out in any desired stages of the dyestuff syntheses.

Particularly valuable dyestuffs of this series are water-soluble azo dyestuffs, and especially those which contain sulphonic acid and/or carboxylic acid groups. The dyestuffs can be either metal-free or metal-containing, the copper, nickel, chromium and cobalt complexes being of preferred interest amongst the metal complexes.

Suitable dyestuff radicals D or the dyestuffs which contain amino groups and on which the dyestuffs of the formula (I) are based are described in a very large number in the literature. Examples which may be mentioned here are:

EP-A 54 515, EP-A 69 703, EP-A 70 807, EP-A 497 174, DE-A 3 222 726, DE-A 2 650 555, DE-A 3 023 855, DE-A 2 847 938, DE-A 2 817 780, GB-A 2 057 479, DE-A 2 916 715, DE-A 2 814 206, DE-A 3 019 936, EP-A 45 488 and Venkataraman: The Chemistry of Synthetic Dyes, volume VI, chapter II, page 211–325, New York, London; 1972. Preferred radicals of an organic dyestuff correspond, for example, to the following groups

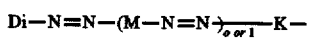

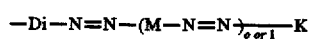

Di represents the radical of a diazo component of the benzene or naphthalene series which is optionally substituted by substituents customary in azo chemistry, in particular hydroxyl, methyl, ethyl, methoxy or ethoxy groups, optionally substituted alkanoylamino groups having 2–4 C atoms, optionally substituted benzoylamino groups or halogen atoms and $SO_2$—Z, K represents the radical of a coupling component of the benzene, naphthalene or ketomethylene series which is optionally substituted by substituents customary in azo chemistry, in particular hydroxyl, amino, methyl, ethyl, methoxy or ethoxy groups, optionally substituted alkanoylamino groups having 2–4 C atoms, optionally substituted benzoylamino groups or halogen atoms, M represents the radical of a central component of the benzene or naphthalene series which is optionally substituted by substituents customary in azo chemistry, in particular hydroxyl, methyl, ethyl, methoxy or ethoxy groups, optionally substituted alkanoyl amino groups having 2–4 C atoms, optionally substituted benzoylamino groups or halogen atoms, and Di, M and K together contain at least two sulphonic acid groups, preferably three to four sulphonic acid groups.

Important azo dyestuffs are, for example, those of the benzene-azo-naphthalene series, the bis-(benzene-azo)-naphthalene series, the benzene-azo-5-pyrazolone series, the benzene-azo-benzene series, the naphthalene-azo-benzene series, the benzene-azo-aminonaphthalene series, the naphthalene-azo-naphthalene series, the naphthalene-azo-5-pyrazolone series, the benzene-azo-pyridone series, the benzene-azo-aminopyridine series, the naphthalene-azo-pyridone series, the naphthalene-azo-amino-pyridine series and the stilbene-azo-benzene series, the dyestuffs containing sulphonic acid groups also being preferred here. In the case of metal complex azo dyestuffs, the groups bonded as a metal complex are preferably in the o-positions relative to the azo group, for example in the form of o,o'-dihydroxy-, o-hydroxy-o'-carboxy-, o-carboxy-o'-amino- and o-hydroxy-o'-amino-azo groupings.

Preferred reactive dyestuffs are those of the formula

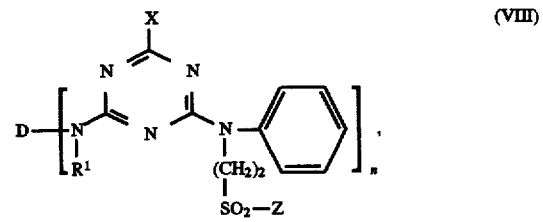

(VII)

wherein

D is the radical of an organic dyestuff of the monoazo, polyazo or metal complex azo series, which contains no further fibre-reactive groups, $R^1$ and $R^2$ independently of one another are H, $CH_3$ or $C_2H_5$, W is a direct bond or bridge member, preferably alkylene or a direct bond i is 0 or 1, j is 0 or 1, X is F or Cl, Z is $CH_2$—$CH_2$—$OSO_3H$ or $CH$=$CH_2$ and n is 1 or 2.

Particularly preferred reactive dyestuffs are those of the formula

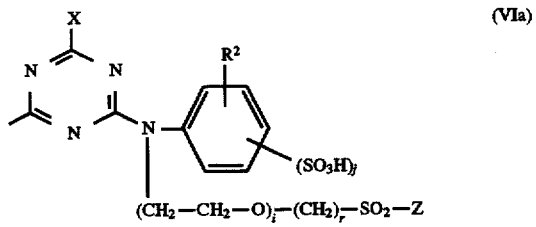

(VIII)

wherein

D is the radical of an organic dyestuff of the monoazo, polyazo or metal complex azo series, which contains no further fibre-reactive groups, X is F, Z is —$CH_2$—$CH_2$—$OSO_3H$, $R^1$ is H and n is 1.

Preferred dyestuffs are those of the following formulae (1) to (42), wherein, generally, B comprises a radical of the formula

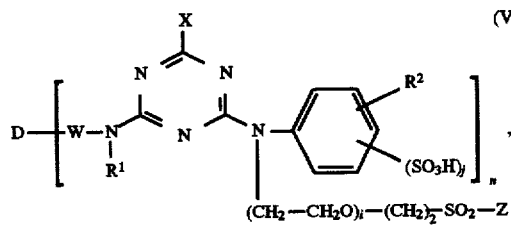

(VIa)

and X, i, $R^2$, j, r and Z have the meaning given for formula (I):

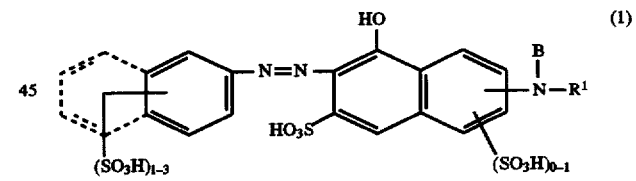

(1)

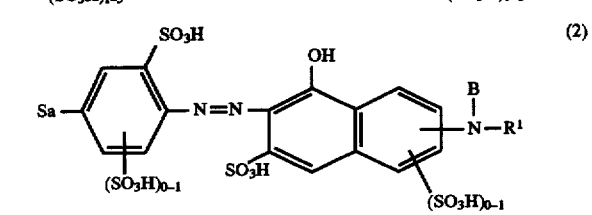

(2)

where Sa=$OCH_3$ or $OC_2H_5$

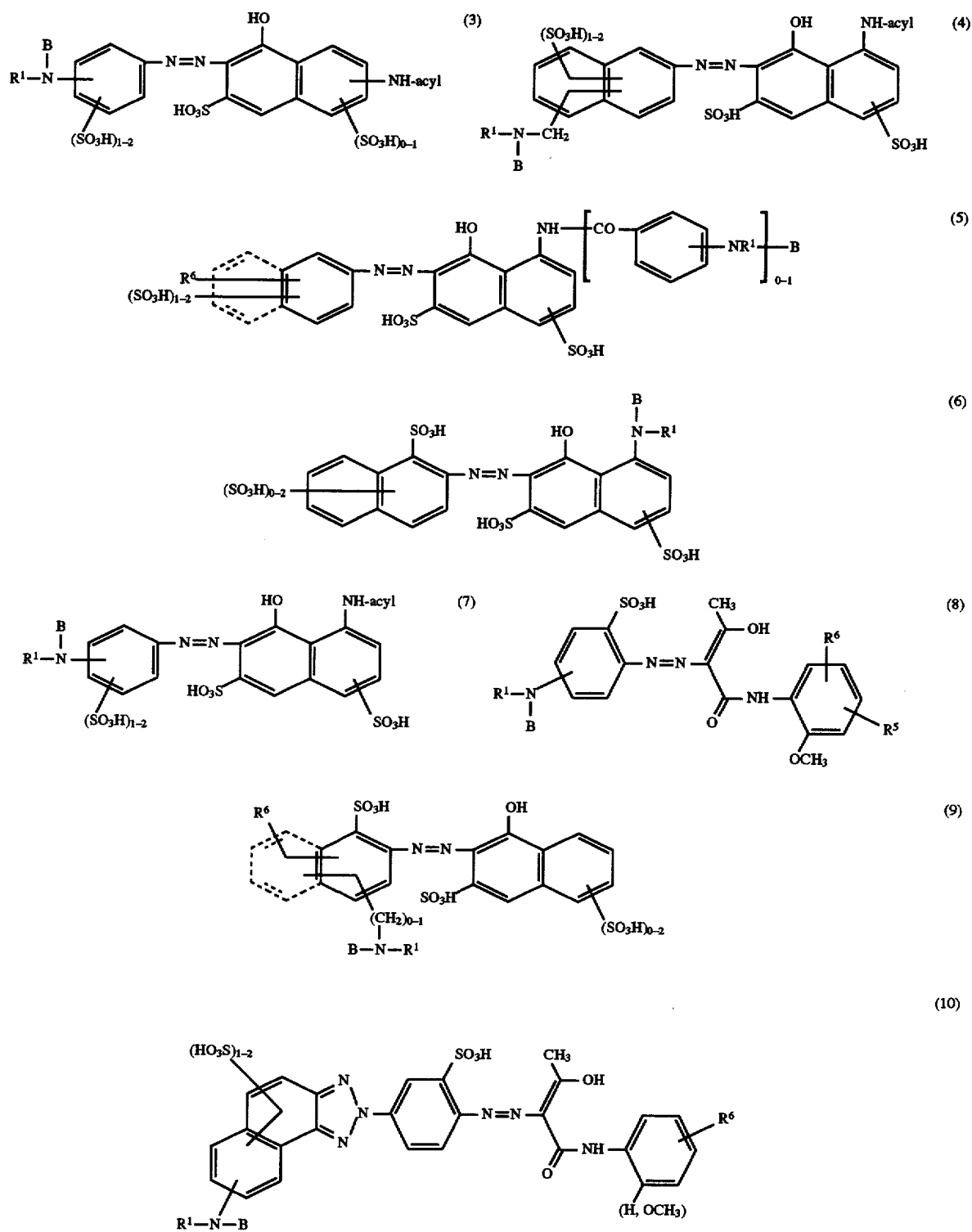

-continued
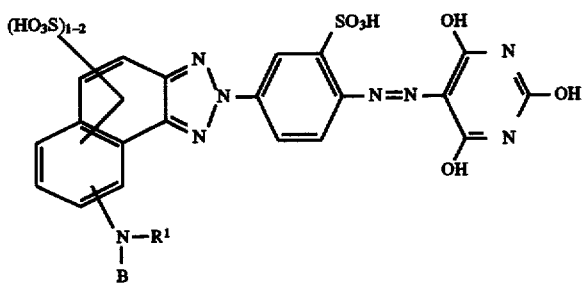
(11)
Metal complexes of dyestuffs of the formulae (12) to (42):
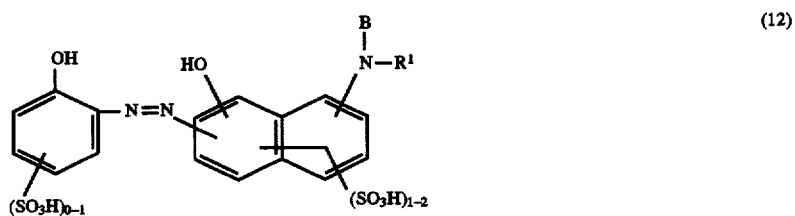
(12)
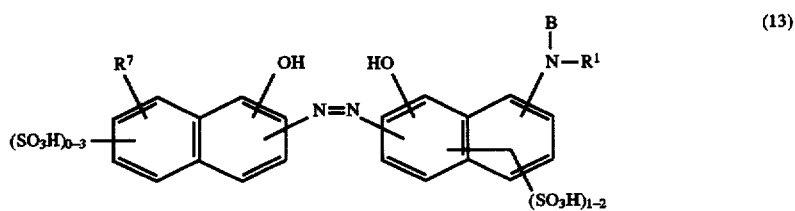
(13)
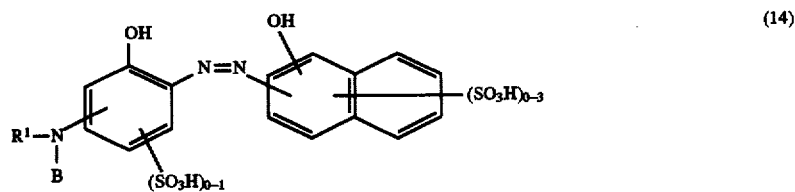
(14)
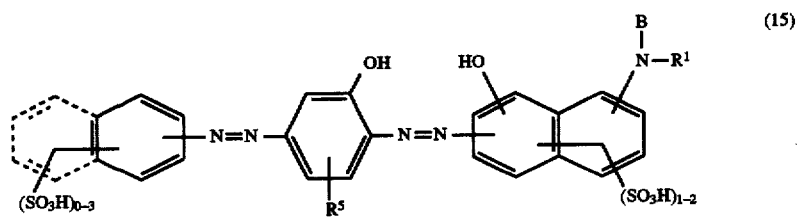
(15)
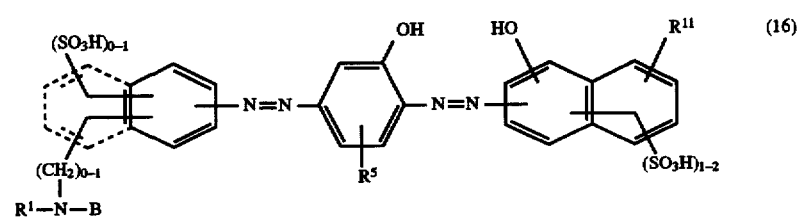
(16)
Cu (1:1 complex) or Cr and Co (1:2 complex) are preferred as the metal atom. Cr and Co complexes can contain one or two molecules of the azo compound of the above-mentioned formula, i.e. they can be built up symmetrically or unsymmetrically with any other desired ligand groups.

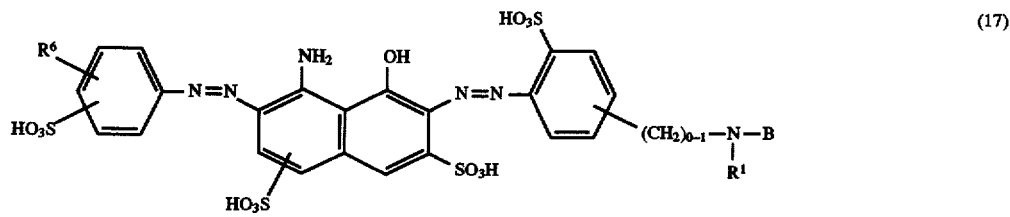
(17)
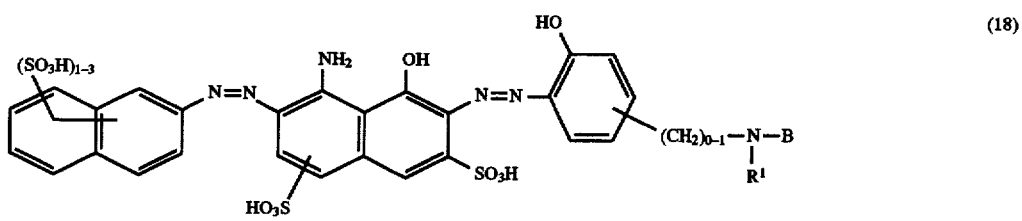
(18)
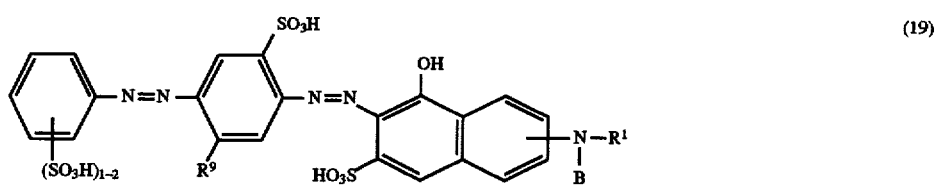
(19)
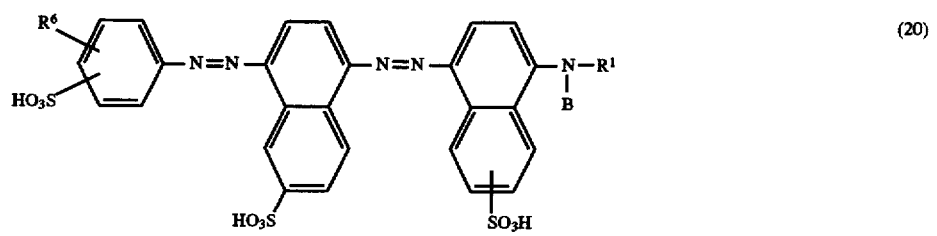
(20)
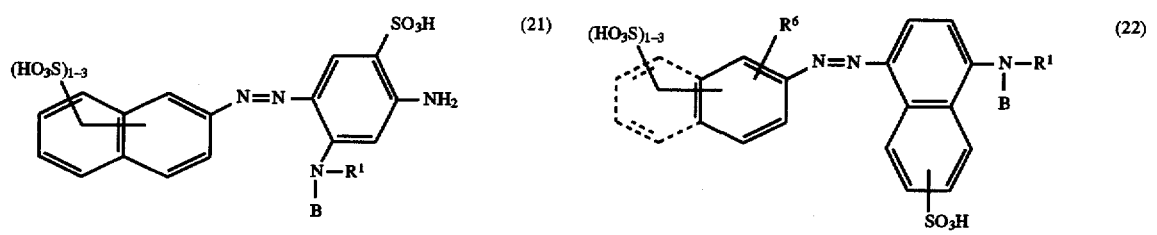
(21) (22)
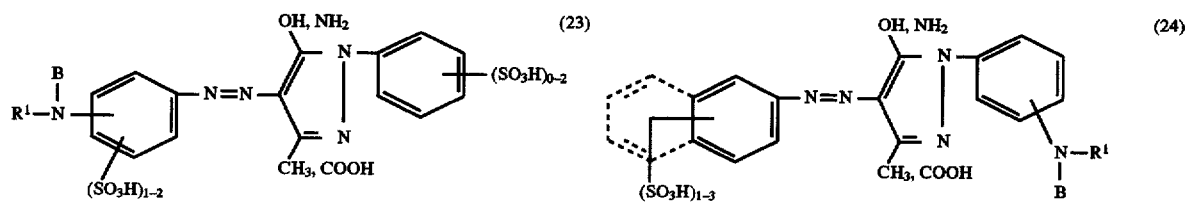
(23) (24)
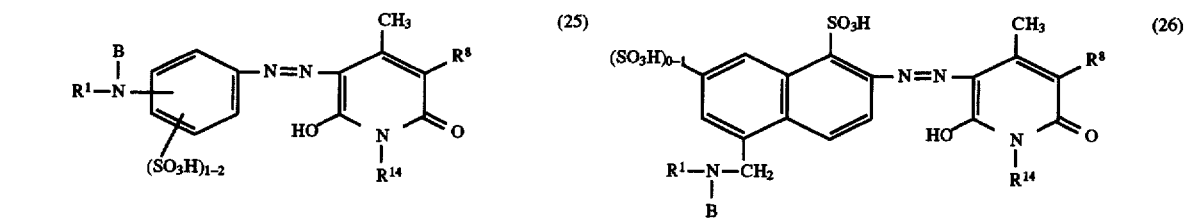
(25) (26)
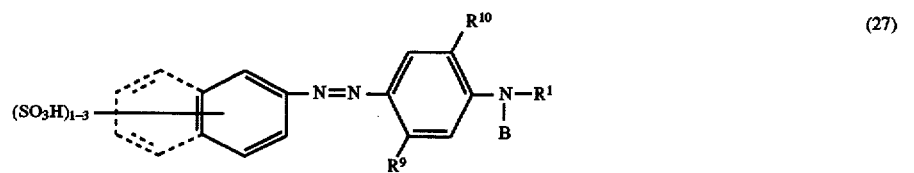
(27)

-continued
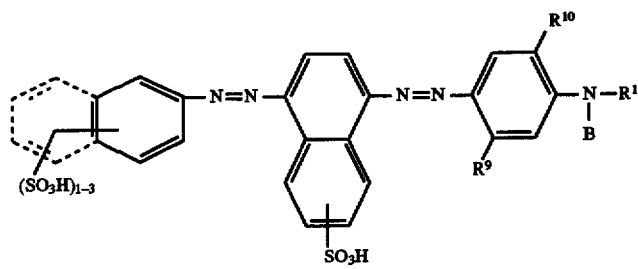
(28)
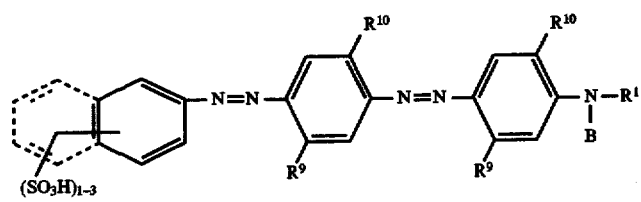
(29)
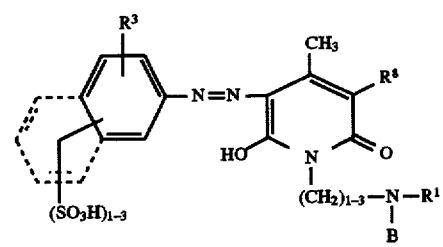
(30)
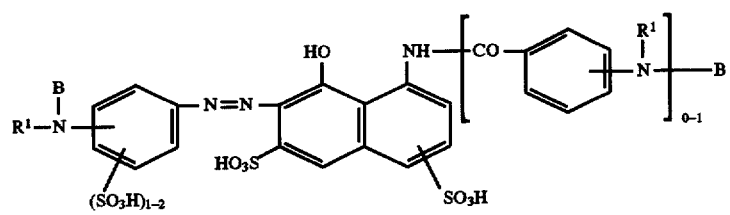
(31)
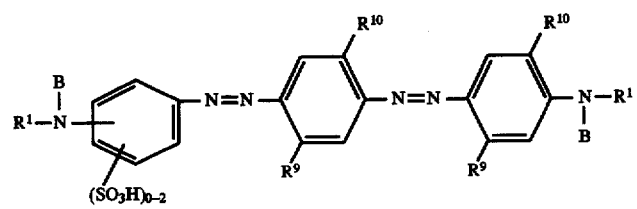
(32)
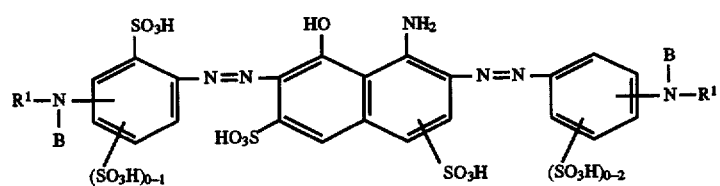
(33)
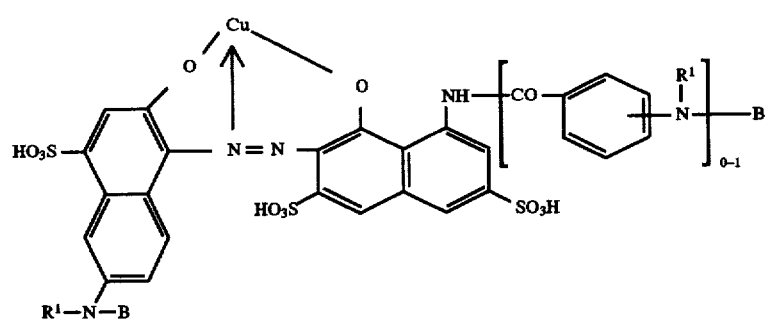
(34)

-continued

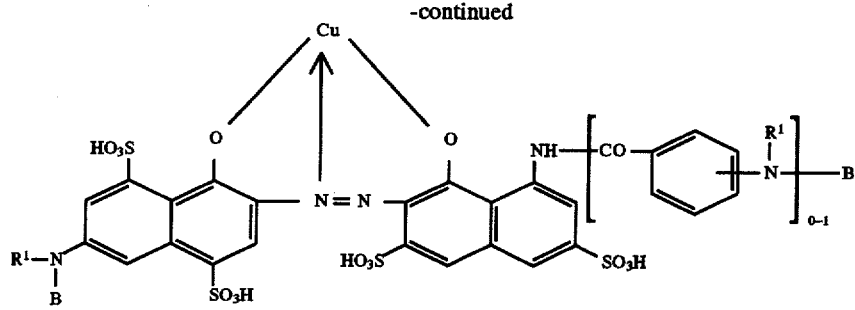
(35)

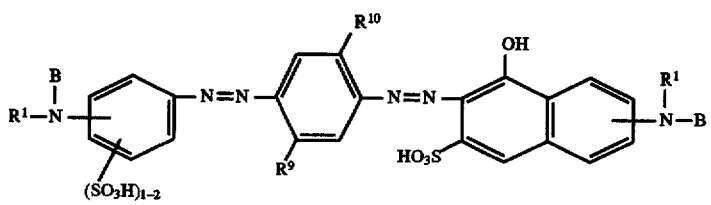
(36)

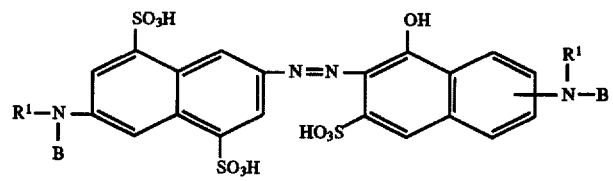
(37)

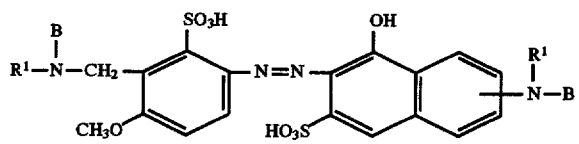
(38)

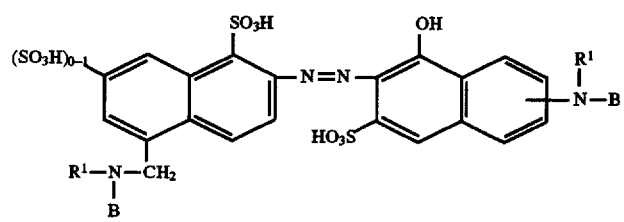
(39)

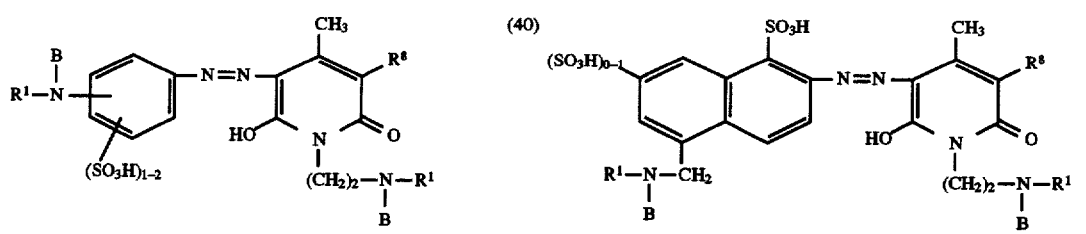
(40) (41)

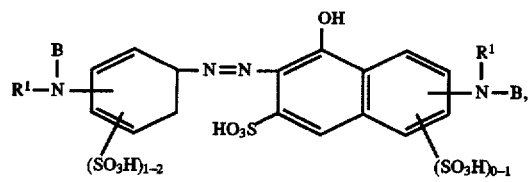
(42)

wherein
  acyl is, for example, acetyl or optionally substituted benzoyl,
  $R^{14}$=H or $C_1$-$C_2$-alkyl which is optionally substituted by $SO_3H$ or $NH_2$,
  $R^1$=H, $CH_3$ or $C_2H_5$,
  $R^3$=H or sulpho,
  $R^5$=H, $CH_3$, $OCH_3$ or Cl,
  $R^6$=H, $C_1$-$C_4$-alkyl, $C_1$-$C_4$-alkoxy, Cl, Br, COOH or $SO_3H$,
  $R^7$=H, OH, $NH_2$, $NHCOCH_3$, NHCOPh, Cl, $C_1$-$C_4$-alkoxy or $C_1$-$C_4$-alkyl,
  $R^8$=H, $SO_3H$, $CH_2SO_3H$, Cl, $C_1$-$C_4$-alkylsulphonyl, CN, carbonamide, in particular $CONH_2$,
  $R^9$=H, $C_1$-$C_4$-alkyl, $C_1$-$C_4$-alkoxy, Cl, Br, acylamino, in particular $C_1$-$C_4$-alkylcarbonylamino or arylcarbonylamino, such as optionally substituted phenylcarbonylamino, $C_1$-$C_4$-alkylsulphonylamino, aminocarbonylamino, $C_1$-$C_4$-alkylsulphonylamino or arylsulphonylamino, and $R^{10}$=H, $C_1$-$C_4$-alkyl, $C_1$-$C_4$-alkoxy, OH or $SO_3H$.

The fused rings indicated by broken lines represent alternatively possible naphthalene systems.

Very particularly preferred reactive dyestuffs are those of the formula (I)
wherein X=Cl, i=0, j=0 or 1, Z=—$CH_2$—$CH_2$—$OSO_3H$, —CH=$CH_2$ or —$CH_2$—$CH_2$—Cl, and $R^2$=H.

Reactive dyestuffs which are likewise very particularly preferred are those of the formula (I),
wherein

X=F, i=0, j=0,

Z=—$CH_2$—$CH_2$—$OSO_3H$, or —CH=$CH_2$, and $R^2$=H and reactive dyestuffs of the formula (I)
wherein

Z=—$CH_2$—$CH_2$—$OSO_3H$.

Also preferred are reactive dyestuffs of the formula (I) wherein the radical D, preferably a radical of an organic dyestuff from the monoazo or polyazo series, is mono- or disubstituted with the group

Z'—$O_2$S—$(CH_2)_{0-1}$ and
wherein

Z' denotes —CH=$CH_2$, —$CH_2$—$CH_2$—$OSO_3H$, —$CH_2$—$CH_2$—Cl, —$CH_2$—$CH_2$—Br , —$CH_2$—$CH_2$—$S_2O_3H$, —$CH_2$—$CH_2$—O—CO—$CH_3$, —$CH_2$—$CH_2$—$OPO_3H_2$ or —$CH_2$—$CH_2$—OH.

Particularly preferred reactive dyestuffs are those of the formula (I)
wherein the radical D, preferably a radical of an organic dyestuff from the monoazo or polyazo series, is mono- or disubstituted with the group

Z'—$O_2$S—$(CH_2)_{0-1}$,

Z' has the above meaning and n=1.

Particularly preferred reactive dyestuffs are also those of the formula (I)
wherein n=1, W=a direct bond and D is a radical of the general formula (IX),

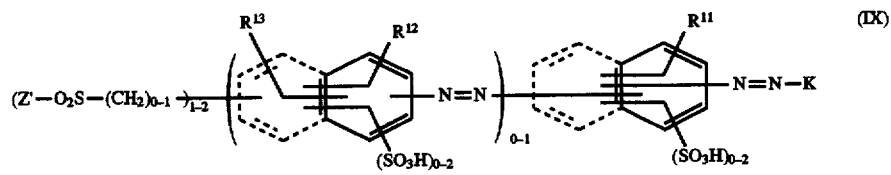

wherein

R$^{11}$ denotes H, C$_1$-C$_4$-alkyl, C$_1$-C$_4$-alkoxy, Cl, Br, acylamino, in particular C$_1$-C$_4$-alkylcarbonylamino or arylcarbonylamino, such as unsubstituted or substituted phenylcarbonylamino, C$_1$-C$_4$-alkylsulphonylamino, aminocarbonylamino, C$_1$-C$_4$-alkylsulphonylamino and arylsulphonylamino, R$^{12}$ denotes H, C$_1$-C$_4$-alkyl, Cl, Br, C$_1$-C$_4$-alkoxy or COOH, R$^{13}$ denotes H, C$_1$-C$_4$-alkyl, C$_1$-C$_4$-alkoxy, SO$_3$H, Cl or Br, K denotes a divalent radical of the general formulae (Xa)-(Xd)

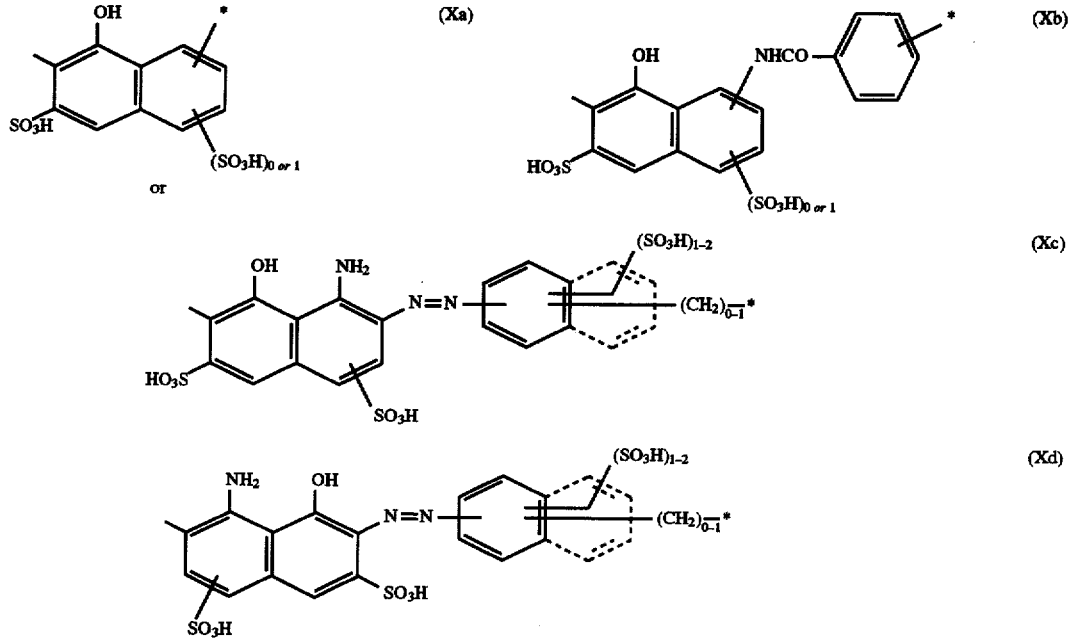

the bonds marked with * being bonds to the group —NR$^1$— B. B has the meaning of formula (VIa).

Particularly preferred radicals Z and Z' are, independently of one another, —CH=CH$_2$ or —C$_2$H$_4$—OSO$_3$H.

Suitable diazo components forming the basis of the radicals D of the formula (IX) for the dyestuffs of the formulae (I) are for example:

aniline-4-β-sulphatoethyl sulphone,
aniline-4-β-thiosulphatoethyl sulphone,
aniline-4-vinyl sulphone,
aniline-3-β-sulphatoethyl sulphone,
aniline-3-vinyl sulphone,
2-methoxy-aniline-5-β-sulphatoethyl sulphone,
2-methoxy-aniline-5-β-thiosulphatoethyl sulphone,
2-methoxyaniline-5-vinyl sulphone,
4-methoxy-aniline-3-β-sulphatoethyl sulphone,
4-methoxy-aniline-3-β-vinyl sulphone,
2,5-dimethoxyaniline-4-β-sulphatoethyl sulphone,
2,5-dimethoxy-aniline-4-vinyl sulphone,
2-methoxy-5-methyl-aniline-4-β-sulphatoethyl sulphone,
aniline-2-β-sulphatoethyl sulphone,
3-(3- or 4-aminobenzoyl)-aminophenyl-β-sulphatoethyl sulphone,
2-methoxy-5-methyl-aniline-4-vinyl sulphone,
6-carboxy-aniline-3-β-sulphatoethyl sulphone,
6-carboxyaniline-3-vinyl sulphone,
2-sulphoaniline-4-β-sulphatoethyl sulphone,
2-sulphoaniline-4-vinyl sulphone,
2,4-disulphoaniline-5-vinyl sulphone,
2-naphthylamine-8-β-sulphatoethyl sulphone,
2-naphthylamine-6-β-sulphatoethyl sulphone,
1-sulpho-2-naphthylamine-6-β-sulphatoethyl sulphone,
1-naphthylamine-4-β-sulphatoethyl sulphone,
1-sulpho-2-naphthylamine-5-β-sulphatoethyl sulphone,
6-sulpho-2-naphthylamine-8-β-sulphatoethyl sulphone,
2-amino-3-sulpho-naphthalene-6,8-bis-(β-sulphatoethyl sulphone),
1-naphthylamine-5-β-sulphatoethyl sulphone,
2-naphthylamine-5-β-sulphatoethyl sulphone,
2-naphthylamine-8-β-sulphatoethyl sulphone,
8-sulpho-2-naphthylamine-6-β-sulphatoethyl sulphone,
4-aminobenzyl-β-sulphatoethyl sulphone,
3-aminobenzyl-β-sulphatoethyl sulphone,
4-aminobenzylvinyl sulphone,
3-aminobenzylvinyl sulphone,
3-amino-4-sulphobenzyl-β-sulphatoethyl sulphone,
4-amino-3-sulphobenzylvinyl sulphone,
2'-(β-sulphatoethylsulphonyl)-3-sulpho-4-aminoazobenzene,
3'-(β-sulphatoethylsulphonyl)-3-sulpho-4-aminoazobenzene,
4'-methoxy-3'-(β-sulphatoethylsulphonyl)-3-sulpho-4-aminoazobenzene,
4'-vinylsulphonyl-2',3-disulpho-4-aminoazobenzene,
2'-(β-sulphatoethylsulphonyl)-6-methyl-3-sulpho-4-aminoazobenzene,
3'-(β-sulphatoethylsulphonyl)-6-methyl-3-sulpho-4-aminoazobenzene,
4'-(β-sulphatoethylsulphonyl)-6-methyl-3-sulpho-4-aminoazobenzene, 4'-(β-sulphatoethylsulphonyl)-2,6-dimethyl-3-sulpho-4-aminoazobenzene,
3'-(β-sulphatoethylsulphonyl)-6-methoxy-3-sulpho-4-aminoazobenzene,
3',4'-bis-(β-sulphatoethylsulphonyl)-6-methoxy-3-sulpho-4-aminoazobenzene,
4'-(β-sulphatoethylsulphonyl)-6-methoxy-3-sulpho-4-aminoazobenzene,
4'-(β-sulphatoethylsulphonyl)-2-methyl-5-methoxy-3-sulpho-4-aminoazobenzene,
4'-(β-sulphatoethylsulphonyl)-2,5-dimethoxy-3-sulpho-4-aminoazobenzene,
3'-(β-sulphatoethylsulphonyl)-2,5-dimethoxy-3-sulpho-4-aminoazobenzene,
2-(4'-amino-3'-sulphophenylazo)-6-(β-sulphatoethylsulphonyl)-naphthalene,
2-(4'-amino-6'-methyl-3'-sulphophenylazo)-1-sulpho-6-(β-sulphatoethylsulphonyl)-naphthalene,
2-(4'-amino-6'-methyl-3'-sulphophenylazo)-6-(β-sulphatoethylsulphonyl)-naphthalene,
2-(4'-amino-3'-sulphophenylazo)-8-sulpho-6-(β-sulphatoethylsulphonyl)-naphthalene, and
2-(4'-amino-6'-methyl-3'-sulphophenylazo)-1,7-disulpho-5-(β-sulphatoethylsulphonyl)-naphthalene.

Examples of suitable coupling components H—K—NHR¹ on which the radicals K are based are:

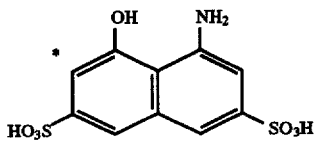

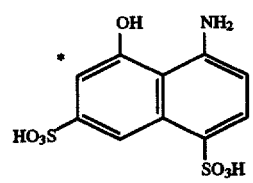

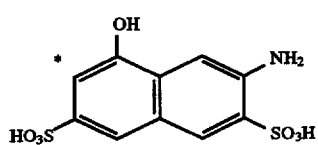

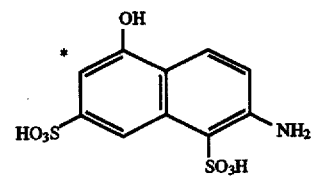

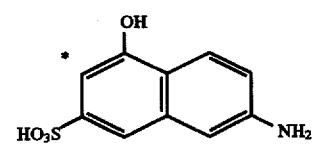

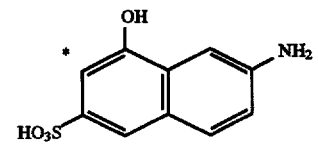

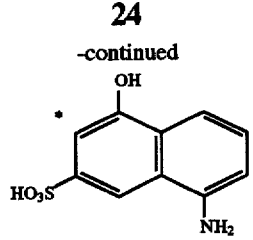

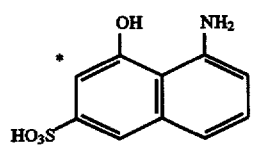

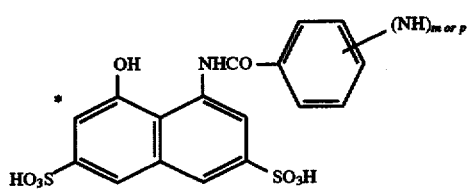

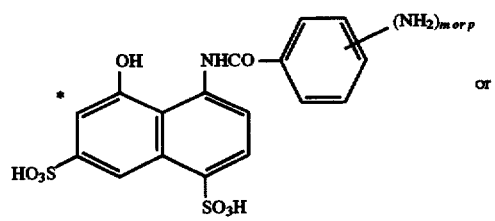

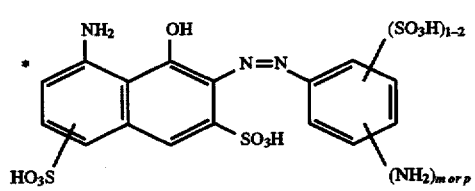

or

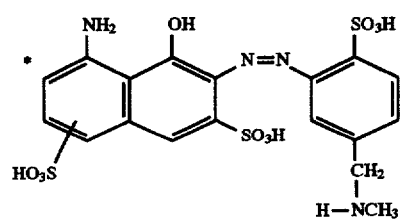

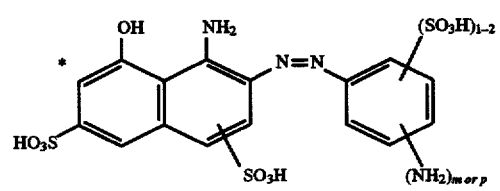

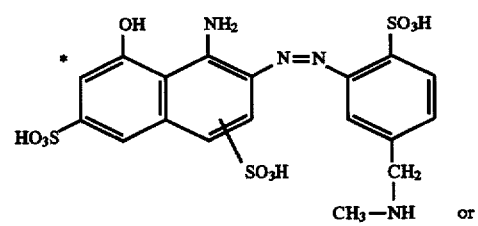

or

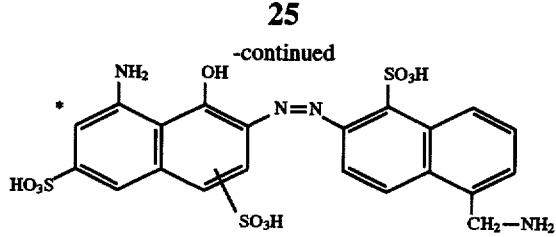

where * marks the coupling site and m or p represents the meta or para position of the amino group with respect to the azo group.

Further preferred reactive dyestuffs are those of the formula (I) having a dyestuff radical D of the formula (IX) wherein $R^1$ and $R^2$=independently of one another H, CH$_3$ or C$_3$H$_5$,
j=0 or 1,
X=F or Cl and
Z and Z'=independently of one another CH$_2$—CH$_2$—OSO$_3$H or CH=CH$_2$.

Particularly preferred reactive dyestuffs of the formula (I) are those having a dyestuff radical D of the formula (IX) wherein $R^1$ and $R^2$=H,
i=0,
j=0,
r=2, and
Z' and Z=—CH$_2$CH$_2$OSO$_3$H.

Preferred dyestuffs within the meaning of formula (I) having a dyestuff radical D of the formula (IX) are those of the following formulae (43) to (52), wherein in general B contains a radical of the formula

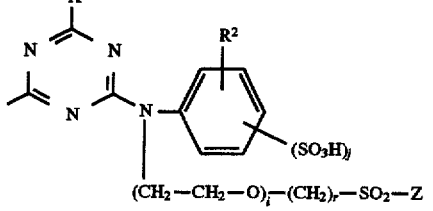

and X, i, $R^2$, j, r and Z have the meaning given above:

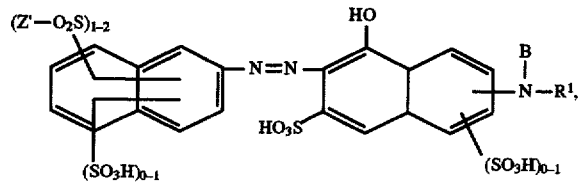

(43)

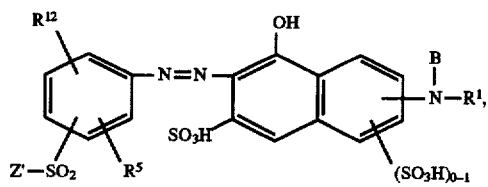

(44)

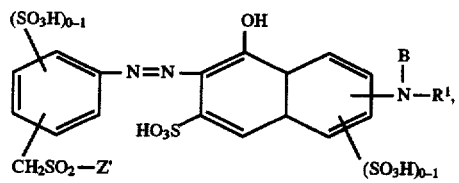

(45)

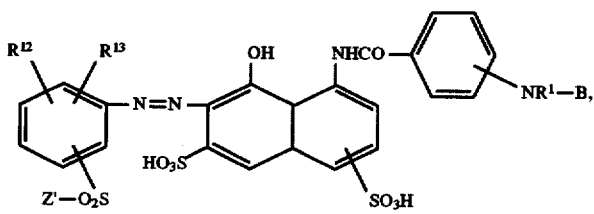

(46)

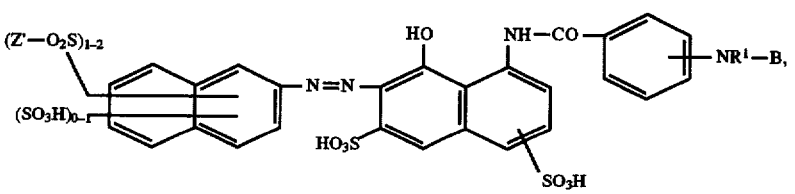

(47)

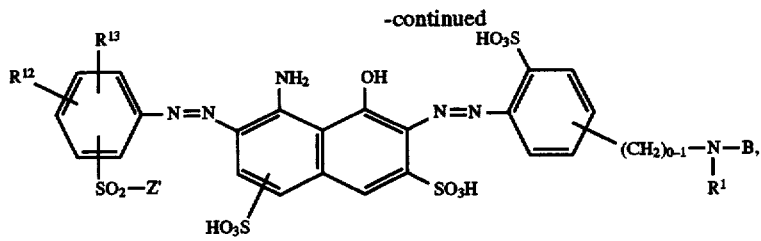
(48)

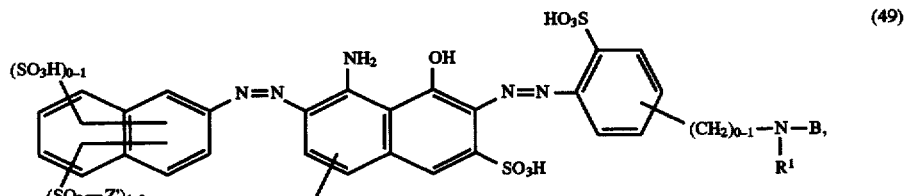
(49)

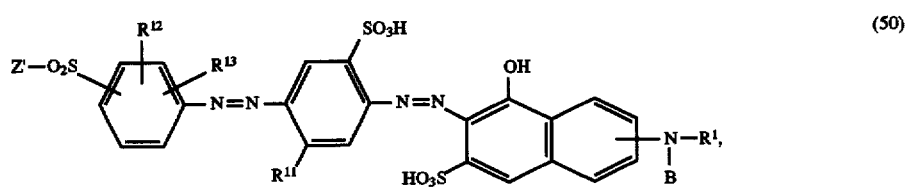
(50)

in which $R^1$=H, $CH_3$ or $C_2H_5$, $R^{11}$=H, $C_1$-$C_4$-alkyl, $C_1$-$C_4$-alkoxy, Cl, Br, acylamino, in particular $C_1$-$C_4$-alkylcarbonylamino or arylcarbonylamino, such as unsubstituted or substituted phenyl carbonylamino, $C_1$-$C_4$-alkylsulphonylamino, aminocarbonylamino, $C_1$-$C_4$-alkylsulphonylamino and arylsulphonylamino, $R^{12}$=H, $C_1$-$C_4$-alkyl, $C_1$-$C_4$-alkoxy, Cl, Br or COOH, and $R^{13}$=H, $C_1$-$C_4$-alkyl, $C_1$-$C_4$-alkoxy, Cl Br or $SO_3H$.

The condensed rings indicated by dashes represent alternatively possible naphthalene systems.

The reactive dyestuffs of the formula (I) are suitable for dyeing and printing the most diverse substrates, such as silk, leather, wool and synthetic polyamide fibres, but in particular cellulose-containing materials having a fibrous structure, such as linen, cellulose, regenerated cellulose and above all cotton. They are suitable both for the exhaustion process and for dyeing by the customary pad-dyeing processes, in which the goods are impregnated with aqueous and if appropriate also salt-containing dyestuff solutions and, after an alkali treatment or in the presence of alkali, the dyestuffs are fixed, if appropriate under the action of heat.

The reactive dyestuffs of the formula (I) are distinguished by a high reactivity and excellent fixing capacity. Because of their bi- or polyfunctionality, they give high fixing yields even from a long liquor. They are characterised by a tinctorial strength which is relatively independent of the dyeing temperature, and can therefore be employed in the exhaustion process at low to moderate dyeing temperatures. In the pad-steam process, they require only short steaming times. They produce dyeings of good depth of colour with good light- and wet-fastness properties.

EXAMPLE 1

A) 0.15 mol of the compound of the formula (for the preparation, see Example 115–118)

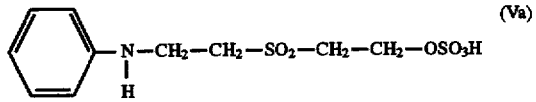
(Va)

were stirred in 100 parts of water and 100 parts of ice and dissolved under neutral conditions. 0.165 mol of 2,4,6-trifluoro-1,3,5-triazine was added dropwise at 0° C. and pH 4–4.5 in the course of 10 minutes. About 250 parts of an aqueous condensation solution having the following structure:

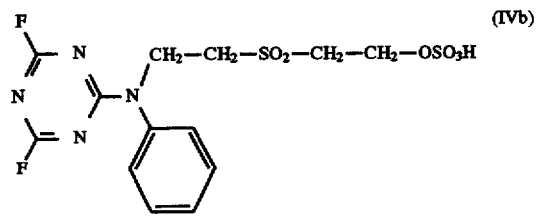
(IVb)

were obtained.

B) 0.1 mol of 1-amino-8-hydroxy-3,6-naphthalenedisulphonic acid was suspended in 150 parts of water and dissolved under neutral conditions with lithium hydroxide solution. 0.1 mol of the above condensation solution was added. A pH of 4–4.5 was maintained at 20° C. with lithium carbonate. The reaction had ended after 8 hours. A solution existed.

C) 0.1 mol of 2-amino-1-naphthalenesulphonic acid was diazotised in a suitable manner and the diazotisation product was coupled to the H-acid condensation product at pH 7.5–8.5. The dyestuff was salted out by addition of potassium chloride and isolated. Drying gave about 35 g of a salt-containing dyestuff coupler, to which the structure

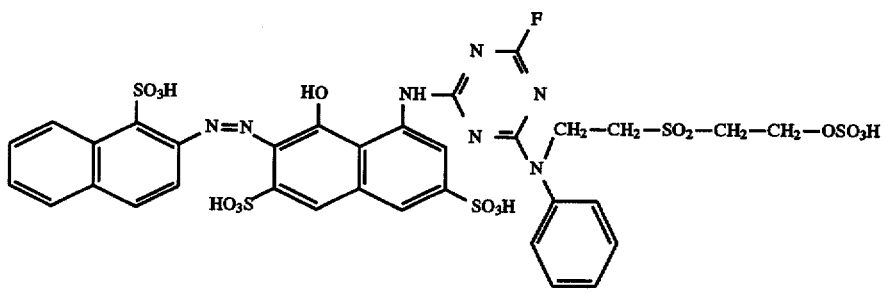

($\lambda_{max}$=521 and 544 nm (H$_2$O)) is attributed and which dyes cotton in red colour shades by the dyeing or printing processes customary for reactive dyestuffs.

EXAMPLE 2

0.1 mol of 2-amino-1,5-naphthalenedisulphonic acid was suspended in 200 parts of water and 100 parts of ice at 0° C. 28 parts of concentrated hydrochloric acid were added. A solution of 7 parts of sodium nitrite in 70 parts of water was added dropwise in the course of 15 minutes. After the mixture had been subsequently stirred for 30 minutes, the diazotisation had ended. A pale yellow suspension resulted. The excess nitrite was destroyed with amidosulphonic acid.

This suspension was now metered into 0.1 mol of the H-acid condensation product from Example 1B over a period of 15–20 minutes. Coupling was carried out at 20° C. and at a pH of 7–8. The dyestuff was precipitated by addition of ethanol and isolated. Drying gave about 40 g of a dyestuff powder, to which the structure

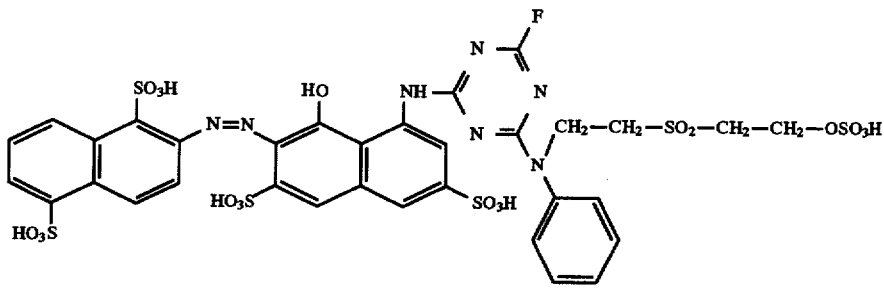

($\lambda_{max}$: 518 and 539 nm (H$_2$O)) is attributed and which dyes cotton in red colour shades by the dyeing and printing processes customary for reactive dyestuffs.

Further red reactive dyestuffs are obtained by condensation of the following components.

| No. | Diazo component | 1-Amino-8-hydroxy-naphthalene-disulphonic acid | Trihalogeno-triazine | Component of the formula (V) | Colour shade | $\lambda_{max}(H_2O)$ |
|---|---|---|---|---|---|---|
| 3 | 2-aminobenzenesulphonic acid (ortho SO₃H, NH₂) | 1-amino-8-hydroxy-2,6-naphthalenedisulphonic acid | 2,4,6-trifluoro-1,3,5-triazine | HN—CH₂—CH₂—SO₂—CH₂—CH₂—OSO₃H, phenyl | red | |
| 4 | 2-aminobenzenesulphonic acid | 1-amino-8-hydroxy-3,5-naphthalenedisulphonic acid | 2,4,6-trifluoro-1,3,5-triazine | HN—CH₂—CH₂—SO₂—CH₂—CH₂—OSO₃H, phenyl | red | |
| 5 | 2-amino-1-naphthalenesulphonic acid | 1-amino-8-hydroxy-3,5-naphthalenedisulphonic acid | 2,4,6-trifluoro-1,3,5-triazine | HN—CH₂—CH₂—SO₂—CH₂—CH₂—OSO₃H, phenyl | bluish-tinged red | |
| 6 | 2-amino-1,5-naphthalenedisulphonic acid | 1-amino-8-hydroxy-3,5-naphthalenedisulphonic acid | 2,4,6-trifluoro-1,3,5-triazine | HN—CH₂—CH₂—SO₂—CH₂—CH₂—OSO₃H, phenyl | red | |
| 7 | 2-amino-5-chlorobenzenesulphonic acid | 1-amino-8-hydroxy-2,6-naphthalenedisulphonic acid | 2,4,6-trifluoro-1,3,5-triazine | HN—CH₂—CH₂—SO₂—CH₂—CH₂—OSO₃H, phenyl | red | |

| No. | Diazo component | 1-Amino-8-hydroxy-naphthalene-disulphonic acid | Trihalogeno-triazine | Component of the formula (V) | Colour shade | $\lambda_{max}(H_2O)$ |
|---|---|---|---|---|---|---|
| 8 | 2-aminotoluene-4-sulphonic acid derivative (SO$_3$H, NH$_2$, H$_3$C substituted benzene) | H-acid (NH$_2$, OH, 2×SO$_3$H naphthalene) | 2,4,6-trifluorotriazine | HN—CH$_2$—CH$_2$—SO$_2$—CH$_2$—CH$_2$—OSO$_3$H (phenyl) | red | |
| 9 | 2-aminonaphthalene-1-sulphonic acid | H-acid | 2,4,6-trichlorotriazine | HN—CH$_2$—CH$_2$—SO$_2$—CH$_2$—CH$_2$—OSO$_3$H (phenyl) | bluish-tinged red | |
| 10 | 2-aminonaphthalene-1,5-disulphonic acid | H-acid | 2,4,6-trichlorotriazine | HN—CH$_2$—CH$_2$—SO$_2$—CH$_2$—CH$_2$—OSO$_3$H (phenyl) | red | |
| 11 | 4-amino-phenyl-β-sulphatoethylsulphone | H-acid | 2,4,6-trifluorotriazine | HN—CH$_2$—CH$_2$—SO$_2$—CH$_2$—CH$_2$—OSO$_3$H (phenyl) | red | |
| 12 | 4-amino-phenyl-β-sulphatoethylsulphone | H-acid | 2,4,6-trichlorotriazine | HN—CH$_2$—CH$_2$—SO$_2$—CH$_2$—CH$_2$—OSO$_3$H (phenyl) | red | |

-continued

| No. | Diazo component | 1-Amino-8-hydroxy-naphthalene-disulphonic acid | Trihalogeno-triazine | Component of the formula (V) | Colour shade | $\lambda_{max}(H_2O)$ |
|---|---|---|---|---|---|---|
| 13 | 2-amino-1-sulfonaphthalene | 1-amino-8-hydroxy-3,6-disulfonaphthalene (1-NH₂, 8-OH, 3-SO₃H, 6-SO₃H) | 2,4,6-trichloro-1,3,5-triazine | HN—C₆H₅, HN—CH₂—CH₂—SO₂—CH₂—CH₂—OSO₃H | bluish-tinged red | |
| 14 | 2-amino-1,5-disulfonaphthalene | 1-amino-8-hydroxy-3,6-disulfonaphthalene | 2,4,6-trichloro-1,3,5-triazine | HN—C₆H₅, HN—CH₂—CH₂—SO₂—CH₂—CH₂—OSO₃H | red | |
| 15 | 4-amino-1-(β-sulfatoethylsulfonyl)benzene | 4-amino-5-hydroxy-2,7-disulfonaphthalene | 2,4,6-trichloro-1,3,5-triazine | HN—C₆H₅, HN—CH₂—CH₂—SO₂—CH₂—CH₂—OSO₃H | red | 533 nm |
| 16 | 2-amino-4-acetylamino-1-sulfobenzene | 1-amino-8-hydroxy-3,6-disulfonaphthalene | 2,4,6-trifluoro-1,3,5-triazine | HN—C₆H₅, HN—CH₂—CH₂—SO₂—CH₂—CH₂—OSO₃H | red | |

-continued

| No. | Diazo component | 1-Amino-8-hydroxy-naphthalene-disulphonic acid | Trihalogeno-triazine | Component of the formula (V) | Colour shade | $\lambda_{max}(H_2O)$ |
|---|---|---|---|---|---|---|
| 17 | 4-aminobenzenesulphonic acid (NH₂, HO₃S on benzene) | 1-amino-8-hydroxy-naphthalene with NH₂, OH, SO₃H, HO₃S | trifluorotriazine | HN—CH₂—CH₂—SO₂—CH₂—CH₂—CH₂—OSO₃H (phenyl) | red | |
| 18 | 2-aminobenzenesulphonic acid (NH₂, SO₃H on benzene) | 1-amino-8-hydroxy-naphthalene with NH—CO—(p-aminophenyl), OH, SO₃H, HO₃S | trifluorotriazine | HN—CH₂—CH₂—SO₂—CH₂—CH₂—CH₂—OSO₃H (phenyl) | red | |

EXAMPLE 19

0.1 mol of the monoazo compound having the formula

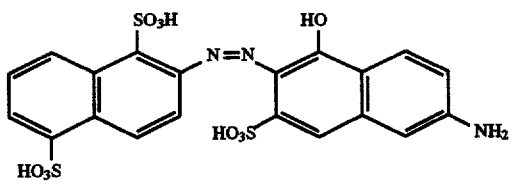

was dissolved in about 500 parts of water under neutral conditions. 0.15 mol of the condensation solution prepared in Example 1 was added. A pH of 7–8 was maintained at 20° C. with sodium carbonate solution. After 2 hours, the reaction had mostly ended. The dyestuff was salted out by addition of potassium chloride, isolated and dried. About 72 g of a salt-containing dyestuff powder were obtained, to which the structure pH 6–6.5 with 10 % strength lithium hydroxide solution. 0.18 mol of the condensation solution prepared in Example 1A was added. A pH of 4–5 was maintained at 20° C. with sodium carbonate solution. The condensation had ended after 2 hours. 900 parts of a solution were obtained. The product was salted out with 180 parts of potassium chloride and isolated. About 220 parts of a grey paste were obtained. The paste was dissolved in 600 parts of water. The above diazotisation mixture was added dropwise, a pH of 6–6.5 being maintained simultaneously by addition of NaHCO$_3$. The pH was then brought to 7.5–8 with sodium carbonate solution. The solution was stirred overnight.

The dyestuff was salted out by addition of sodium chloride and isolated. Drying gave about 105 g of a salt-containing dyestuff powder, to which the structure

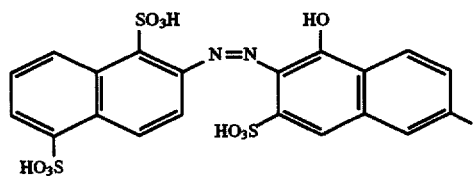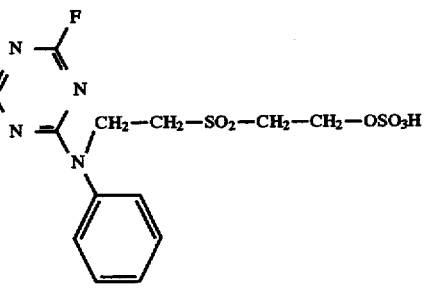

($\lambda_{max}$=485 nm (H$_2$O)) is attributed and which dyes cotton in orange colour shades by the dyeing or printing processes customary for reactive dyestuffs.

EXAMPLE 20

0.1 mol of 2-amino-5-methoxy-benzenesulphonic acid was dissolved in 150 parts of water and 50 parts of ice under neutral conditions. 28 parts of concentrated hydrochloric

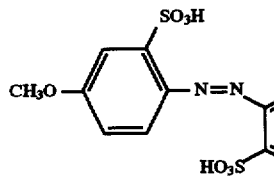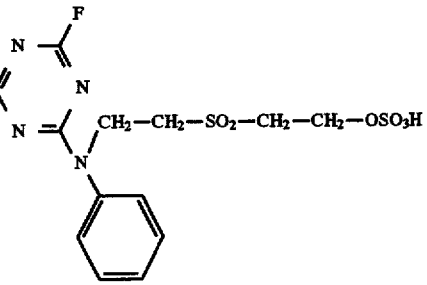

acid were added. A solution of 7 parts of sodium nitrite in 70 parts of water was added dropwise in the course of 15 minutes. After the mixture had been subsequently stirred for 30 minutes, the diazotisation had ended. The excess nitrite was destroyed with amidosulphonic acid.

0.12 mol of 7-amino-4-hydroxy-naphthalene-2-sulphonic acid was suspended in 300 parts of water and dissolved at is attributed, and which dyes cotton in scarlet shades by the dyeing or printing processes customary for reactive dyestuffs.

Further reactive dyestuffs are obtained by condensation of trifluorotriazine and the following components analogously to Example 19 or 20.

| No. | Azo component | Component of the formula (V) | Colour shade |
|---|---|---|---|
| 20a | 1-SO₃H-naphthyl—N=N—(2-HO₃S, 1-OH, 6-NH₂-naphthalene) | HN—C₆H₄—CH₂—CH₂—SO₂—CH₂—CH₂OSO₃H | orange |
| 21 | (4,8-disulfo)naphthyl—N=N—(2-HO₃S, 1-OH, 6-NH₂-naphthalene) | HN—C₆H₄—CH₂—CH₂—SO₂—CH₂—CH₂OSO₃H | orange |
| 22 | (5-SO₃H)naphthyl—N=N—(2-HO₃S, 1-OH, 6-NHCH₃-naphthalene) | HN—C₆H₄—CH₂—CH₂—SO₂—CH₂—CH₂OSO₃H | orange |
| 23 | (2,5-disulfo-4-methoxy)phenyl—N=N—(2-HO₃S, 1-OH, 6-NH₂-naphthalene) | HNCH₂C₆H₄—SO₂—CH₂—CH₂OSO₃H | orange |
| 24 | (2,5-disulfo-4-methyl)phenyl—N=N—(2-HO₃S, 1-OH, 6-NH₂-naphthalene) | HNCH₂C₆H₄—SO₂—CH₂—CH₂OSO₃H | orange |

-continued

| No. | Azo component | Component of the formula (V) | Colour shade |
|---|---|---|---|
| 25 | [structure: naphthalene with OH, NH2, HO3S, N=N to benzene with SO3H, SO3H, H3C] | HNCH2CH2—SO2—CH2—CH2OSO3H—phenyl | orange |
| 26 | [structure: naphthalene with OH, NH2, HO3S, N=N to benzene with SO3H, N=N to phenyl with HO3S] | HNCH2CH2—SO2CH2CH2OSO3H—phenyl | yellowish-tinged red |
| 27 | [structure: naphthalene with OH, NH2, HO3S, N=N to benzene with SO3H, N=N to phenyl with SO3H, HO3S] | HNCH2CH2—SO2CH2CH2OSO3H—phenyl | yellowish-tinged red |
| 28 | [structure: naphthalene with OH, NH2, HO3S, N=N to phenyl with HO3S—OH2C—CH2—O2S] | HNCH2CH2—SO2CH2CH2OSO3H—phenyl | yellowish-tinged red |
| 29 | [structure: naphthalene with OH, NH2, SO3H, HO3S, N=N to naphthalene with SO3H] | HNCH2CH2—SO2—CH2—CH2OSO3H—phenyl | orange |

-continued

| No. | Azo component | Component of the formula (V) | Colour shade |
|---|---|---|---|
| 30 | SO₃H-naphthalene-OH-N=N-naphthalene(HO₃S)(NH₂), with SO₃H on other naphthalene ring | HNCH₂CH₂—SO₂—CH₂—CH₂OSO₃H on phenyl | scarlet |
| 31 | SO₃H-naphthalene-OH-N=N-naphthalene(HO₃S)(NH₂), with SO₂—CH₂—CH₂OSO₃H on other naphthalene ring | HNCH₂CH₂—SO₂—CH₂—CH₂OSO₃H on phenyl | scarlet |

EXAMPLE 32

0.1 mol of the monoazo dyestuff of the formula

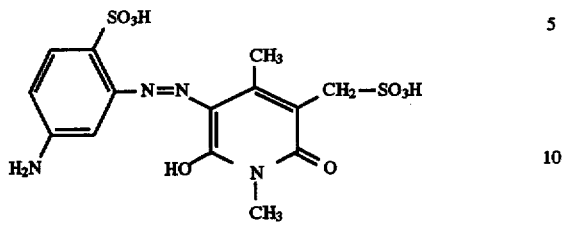

was dissolved in 500 parts of water under neutral conditions. 0.2 mol of the condensation solution prepared in Example 1A was added. A pH of 7–8 was maintained over hours at 20° C. with sodium carbonate solution. About parts of a dyestuff solution were obtained. The dyestuff was salted out with potassium chloride, isolated and dried. About 105 g of a salt-containing dyestuff powder were obtained, to which the structure

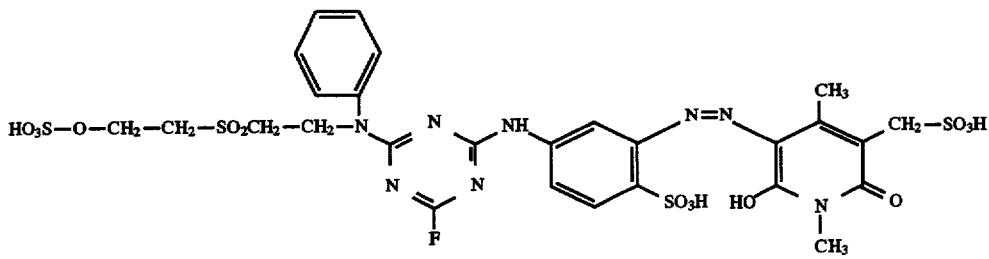

($\lambda_{max}$=420 nm (H$_2$O)) is attributed and which dyes cotton in yellow colour shades by the dyeing or printing processes customary for reactive dyestuffs.

Further yellow reactive dyestuffs are obtained by condensation of the following components:

| No. | Azo component | Trihalogeno-triazine | Component of the formula (V) | Colour shade | $\lambda_{max}$ (H$_2$O) |
|---|---|---|---|---|---|
| 33 | (pyridone azo with CH$_3$, CH$_2$—SO$_3$H, N—C$_2$H$_5$, OH; phenyl with SO$_3$H, H$_2$N) | trifluorotriazine | HN—CH$_2$—CH$_2$—SO$_2$—CH$_2$—CH$_2$—Cl | greenish-tinged yellow | |
| 34 | (pyridone azo with CH$_3$, CONH$_2$, N—CH$_2$—CH$_2$—SO$_3$H, OH; phenyl with SO$_3$H, H$_2$N) | trifluorotriazine | HN—CH$_2$—CH$_2$—SO$_2$—CH$_2$—CH$_2$—OSO$_3$H | greenish-tinged yellow | |
| 35 | (pyridone azo with CH$_3$, N—CH$_3$, OH; phenyl with SO$_3$H, SO$_3$H, H$_2$N) | trifluorotriazine | HN—CH$_2$—CH$_2$—SO$_2$—CH$_2$—CH$_2$—OSO$_3$H | yellow | |
| 36 | (pyridone azo with CH$_3$, CH$_2$—SO$_2$H, N—CH$_3$, OH; phenyl with SO$_3$H, H$_2$N) | trifluorotriazine | HN—CH$_2$—CH$_2$—SO$_2$—CH$_2$—CH$_2$—OSO$_3$H | yellow | |

-continued

| No. | Azo component | Trihalogeno-triazine | Component of the formula (V) | Colour shade | $\lambda_{max}$ (H$_2$O) |
|---|---|---|---|---|---|
| 37 | [azo component with CH$_3$, CONH$_2$, N-C$_2$H$_5$, HO, SO$_3$H, H$_2$N-phenyl] | F,F,F-triazine | HN—CH$_2$—CH$_2$—SO$_2$—CH$_2$—CH$_2$OSO$_3$H with phenyl | greenish-tinged yellow | |
| 38 | [azo component with CH$_3$, CH$_2$—SO$_3$H, N-C$_2$H$_5$, HO, SO$_3$H, H$_2$N-phenyl] | F,F,F-triazine | HN—CH$_2$—CH$_2$—SO$_2$—CH$_2$—CH$_2$OSO$_3$H with phenyl | greenish-tinged yellow | |
| 39 | [azo component with CH$_3$, CH$_2$—SO$_3$H, N-CH$_3$, HO, SO$_3$H, H$_2$N-phenyl] | F,F,F-triazine | HN—CH$_2$—CH$_2$SO$_2$—CH=CH$_2$ with phenyl | greenish-tinged yellow | |
| 40 | [azo component with CH$_3$, CH$_2$—SO$_3$H, N-CH$_3$, HO, SO$_3$H, H$_2$N-phenyl] | Cl,Cl,Cl-triazine | HN—CH$_2$—CH$_2$SO$_2$—CH=CH$_2$ with phenyl | greenish-tinged yellow | |
| 41 | [azo component with CH$_3$, CONH$_2$, N-CH$_3$, HO, SO$_3$H, HN—CH$_2$—CH$_3$ phenyl] | F,F,F-triazine | HNCH$_2$CH$_2$SO$_2$CH$_2$CH$_2$OSO$_3$H with phenyl | greenish-tinged yellow | |

-continued

| No. | Azo component | Trihalogeno-triazine | Component of the formula (V) | Colour shade | $\lambda_{max}$ (H$_2$O) |
|---|---|---|---|---|---|
| 42 | (2-SO$_3$H phenyl)-N=N-(pyridone with CH$_3$, CH$_3$, CH$_2$-SO$_3$H, N-CH$_3$, OH; with HN-CH$_2$-CH$_3$ substituent) | 2,4,6-trifluorotriazine | HNCH$_2$CH$_2$SO$_2$CH$_2$CH$_2$OSO$_3$H — phenyl | greenish-tinged yellow | |
| 43 | (2-SO$_3$H, 5-H$_2$N phenyl)-N=N-(pyridone with CH$_3$, CH$_3$, CH$_2$-SO$_3$H, N-C$_2$H$_5$, OH) | 2,4,6-trichlorotriazine | HNCH$_2$CH$_2$SO$_2$CH$_2$CH$_2$OSO$_3$H — phenyl | greenish-tinged yellow | 421 nm |
| 44 | (1,5-di-SO$_3$H naphthyl)-N=N-(pyridone with CH$_3$, CONH$_2$, OH, N-CH$_2$-CH$_2$-NH$_2$, =O) | 2,4,6-trichlorotriazine | HNCH$_2$CH$_2$SO$_2$CH$_2$CH$_2$OSO$_3$H — phenyl | yellow | |

EXAMPLE 45

0.1 mol of the monoazo dyestuff of the formula

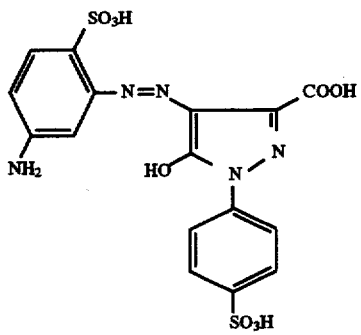

was dissolved in 400 parts of water under neutral conditions. 0.15 mol of the condensation solution prepared in Example 1A was added. A pH of 7–8 was maintained over 8 hours at 20° C. with sodium carbonate solution. About 1100 parts of a dyestuff solution were obtained. The dyestuff was salted out with potassium chloride, isolated and dried. About 105 g of a salt-containing dyestuff powder were obtained, to which the structure

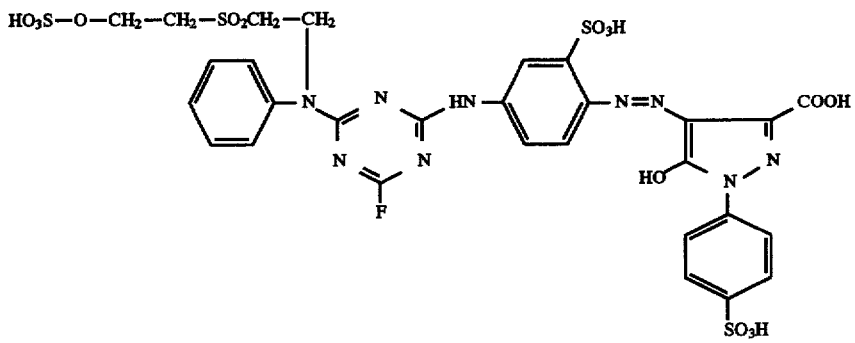

is attributed and which ayes cotton in yellow colour shades by the dyeing or printing processes customary for reactive dyestuffs.

Further yellow dyestuffs having similar properties are obtained if the following aminophenylazopyrazolones are subjected to a condensation reaction with cyanuric fluoride and the compound of the formula (V) shown.

| No. | Aminophenylazopyrazolone | Component of the formula (V) |
|---|---|---|
| 46 | 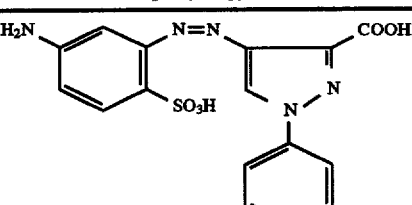 | $HN-CH_2-CH_2-SO_2-CH_2-CH_2OSO_3H$ <br/> (phenyl) |
| 47 | 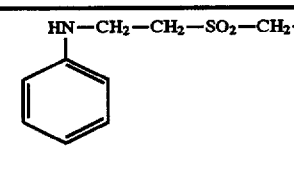 | $HN-CH_2-CH_2-SO_2-CH_2-CH_2OSO_3H$ <br/> (phenyl) |

-continued

| No. | Aminophenylazopyrazolone | Component of the formula (V) |
|---|---|---|
| 48 | H₂N–C₆H₃(SO₃H)–N=N–C(COOH)=C(OH)–N(N-C₆H₄-SO₃H) pyrazolone | HN—CH₂—CH₂—SO₂—CH₂—CH₂OSO₃H (phenyl) |
| 49 | H₂N–C₆H₃(SO₃H)–N=N–pyrazolone(CH₃,OH) with N–naphthyl-4,8-disulfonic acid | HN—CH₂—CH₂—SO₂—CH₂—CH₂OSO₃H (phenyl) |
| 50 | H₂N–C₆H₃(SO₃H)–N=N–pyrazolone(CH₃,OH), NH | HN—CH₂—CH₂—SO₂—CH₂—CH₂OSO₃H (phenyl) |
| 51 | H₂N–C₆H₃(SO₃H)–N=N–pyrazolone(CH₃,OH) with N-(2-Cl-5-SO₃H-phenyl) | HN—CH₂—CH₂—SO₂—CH₂—CH₂OSO₃H (phenyl) |
| 52 | H₂N–C₆H₃(SO₃H)–N=N–pyrazolone(CH₃,OH) with N-(2-SO₃H-4-SO₃H-phenyl) | HN—CH₂—CH₂—SO₂—CH₂—CH₂OSO₃H (phenyl) |

EXAMPLE 53

45.3 g of the coupling product of 2-aminonaphthalene-6,8-disulphonic acid on 3-aminoacetanilide are dissolved in 600 ml of water at pH 7, while heating at 50° C. After cooling to 20° C., 0.15 mol of component (VIb), prepared according to Example 1A, of the formula

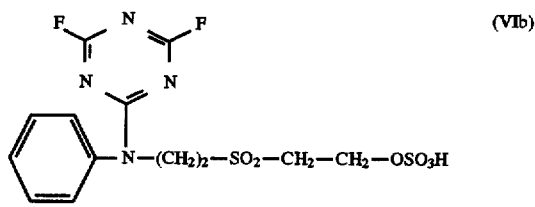

(VIb)

is added, and the pH is maintained at 7–7.5 for 8 hours with sodium carbonate solution.

The resulting solution is evaporated in vacuo at 35° to 40° C. or spray dried, after addition of 1.5 g of phosphate buffer of pH 6.

The resulting dyestuff of the formula

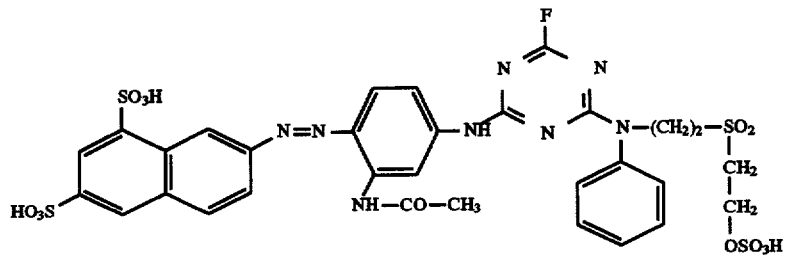

dyes cotton in golden yellow shades from a long liquor at an optimum dyeing temperature of 50° C. $\lambda_{max}$=389 nm in water.

Further dyestuffs which give reddish-tinged yellow dyeings are obtained by condensation of the following p-aminoazo compounds with cyanuric fluoride or cyanuric chloride and compounds of the formula (V).

| No. | Azo component | Trihalogeno-triazine | Component of the formula (V) | Colour shade |
|---|---|---|---|---|
| 54 | naphthalene with SO3H, SO3H, HO3S, N=N to phenyl with NH2 and NH—CO—NH2 | 2,4,6-trifluoro-triazine | HNCH2CH2—SO2—CH2—CH2OSO3H— phenyl | reddish-tinged yellow |
| 55 | naphthalene with SO3H, HO3S, N=N to phenyl with NH2 and NH—CONH2 | 2,4,6-trifluoro-triazine | HNCH2CH2—SO2—CH2—CH2OSO3H— phenyl | reddish-tinged yellow |
| 56 | naphthalene with SO3H, SO3H, N=N to phenyl with NH2 and NH—COCH3 | 2,4,6-trifluoro-triazine | HNCH2CH2—SO2—CH2—CH2OSO3H— phenyl | reddish-tinged yellow |
| 57 | naphthalene with SO3H, SO3H, N=N to phenyl with NH2 and NH—CO—NH2 | 2,4,6-trifluoro-triazine | HNCH2CH2—SO2—CH2—CH2OSO3H— phenyl | reddish-tinged yellow |
| 58 | naphthalene with SO3H, SO3H, HO3S, N=N to phenyl with NH2 and NH—COCH3 | 2,4,6-trifluoro-triazine | HNCH2CH2—SO2—CH2—CH2OSO3H— phenyl | reddish-tinged yellow |

| No. | Azo component | Trihalogeno-triazine | Component of the formula (V) | Colour shade |
|---|---|---|---|---|
| 59 | naphthalene-1,5-disulfonic acid with -N=N- to phenyl(CH₃)(NH₂) | 2,4,6-trifluoro-triazine | HNCH₂CH₂—SO₂—CH₂—CH₂OSO₃H phenyl | reddish-tinged yellow |
| 60 | SO₃H-phenyl-N=N-phenyl(NH₂)(NHCOCH₃)(SO₃H) | 2,4,6-trifluoro-triazine | HNCH₂CH₂—SO₂—CH₂—CH₂OSO₃H phenyl | reddish-tinged yellow |
| 61 | SO₃H-phenyl-N=N-phenyl(NH₂)(NHCOCH₃)(SO₃H) | 2,4,6-trifluoro-triazine | HNCH₂CH₂—SO₂—CH₂—CH₂OSO₃H phenyl | reddish-tinged yellow |
| 62 | SO₃H-phenyl-N=N-phenyl(NH₂)(NHCOCH₃)(SO₃H) | 2,4,6-trichloro-triazine | HNCH₂CH₂—SO₂—CH₂—CH₂OSO₃H phenyl | reddish-tinged yellow |
| 63 | naphthalene-1,5-disulfonic acid with -N=N- to phenyl(NH₂)(NHCOCH₃) | 2,4,6-trifluoro-triazine | HNCH₂CH₂—SO₂—CH₂—CH₂—Cl phenyl | reddish-tinged yellow |

-continued

| No. | Azo component | Trihalogeno-triazine | Component of the formula (V) | Colour shade |
|---|---|---|---|---|
| 64 | (naphthalene with SO₃H, HO₃S, SO₃H substituents)—N=N—(phenyl)—N=N—(phenyl-NH₂) | 2,4,6-trifluorotriazine | HNCH₂CH₂—SO₂—CH₂—CH₂—Cl with phenyl | orange |
| 65 | (naphthalene with SO₃H, SO₃H, HO₃S)—N=N—(phenyl with NH₂ and NH—COCH₃) | 2,4,6-trichlorotriazine | HNCH₂CH₂—SO₂—CH₂CH₂OSO₃H with phenyl | reddish-tinged yellow |
| 66 | (naphthalene with SO₃H, SO₃H)—N=N—(phenyl with NH₂ and CH₃) | 2,4,6-trichlorotriazine | HNCH₂CH₂—SO₂—CH₂CH₂OSO₃H with phenyl | reddish-tinged yellow |
| 67 | (naphthalene with SO₃H, HO₃S)—N=N—(phenyl with NH₂ and NH—CO—CH₃) | 2,4,6-trichlorotriazine | HNCH₂CH₂—SO₂—CH₂—CH₂OSO₃H with phenyl | reddish-tinged yellow |
| 68 | (naphthalene with SO₃H, SO₃H, HO₃S)—N=N—(phenyl with NH₂ and NH—CO—CH₃) | 2,4,6-trichlorotriazine | HNCH₂CH₂—SO₂—CH₂—CH₂OSO₃H with phenyl | reddish-tinged yellow |

EXAMPLE 69

0.15 mol of the component of the formula

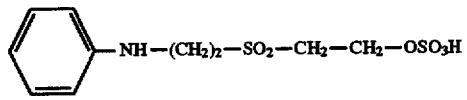

is subjected to a condensation reaction with cyanuric fluoride according to Example 17. The resulting solution of the condensation product is allowed to run into a solution, adjusted to pH 7 and cooled to 0° to 5° C., of 0.1 mol of the azo compound of the formula

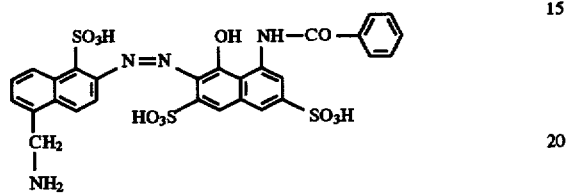

in 300 ml of water, during which the pH in the mixture is maintained at 6.5–7.5 with dilute sodium carbonate solution. The temperature rises to 20°–25° C. When the condensation has ended, the dyestuff is isolated by salting out and filtration with suction and, after buffering to pH 6.5, is dried in vacuo at 45° C. It corresponds to the formula

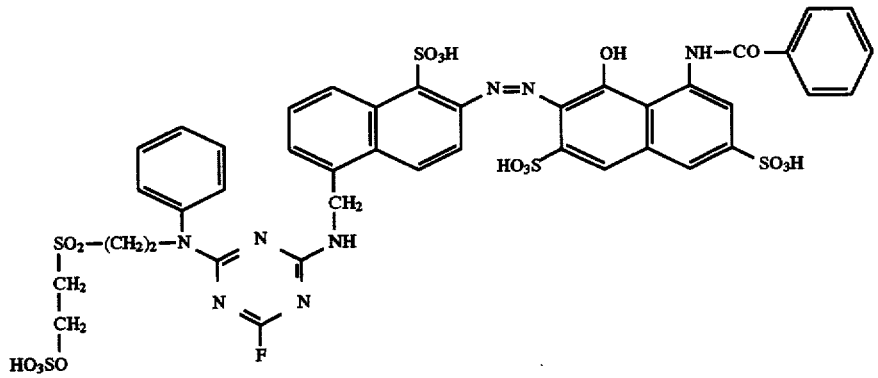

and dyes cotton in bluish-tinged red shades from a long liquor with a good fixing yield.

Similar red dyestuffs are obtained by reaction of the following components.

| No. | Diaminobenzenesulphonic acid | Trihalogenotriazine | Coupling component | Component of the formula (V) | Colour shade |
|---|---|---|---|---|---|
| 70 | 4-amino-aniline with NH₂ and SO₃H (2-amino-4-sulpho) | F,F,F-triazine | 8-OH,NH-CO-phenyl naphthalene with SO₃H, HO₃S | HNCH₂CH₂—SO₂—CH₂—CH₂OSO₃H | red |
| 71 | similar diaminobenzenesulphonic acid | F,F,F-triazine | 8-OH,NH-CO-phenyl naphthalene with SO₃H, HO₃S | HNCH₂CH₂—SO₂—CH₂—CH₂OSO₃H | bluish-tinged red |
| 72 | similar diaminobenzenesulphonic acid | F,F,F-triazine | 8-OH,NH-COCH₃ naphthalene with SO₃H, HO₃S | HNCH₂CH₂—SO₂—CH₂—CH₂OSO₃H | red |
| 73 | CH₃-substituted diaminobenzenesulphonic acid | F,F,F-triazine | 8-OH,NH-CO-C₂H₅ naphthalene with SO₃H, HO₃S | HNCH₂CH₂—SO₂—CH₂—CH₂OSO₃H | red |

| No. | Azo component | Trihalogenotriazine | Component of the formula (V) | Colour shade |
|---|---|---|---|---|
| 74 | naphthalene-azo-naphthalene with OH, NH-COCH₃, SO₃H, HO₃S, CH₂-*NH₂ | F,F,F-triazine | HNCH₂CH₂—SO₂—CH₂—CH₂—Cl | red |

-continued
| No. | | | | Colour shade |
|---|---|---|---|---|
| 75 | 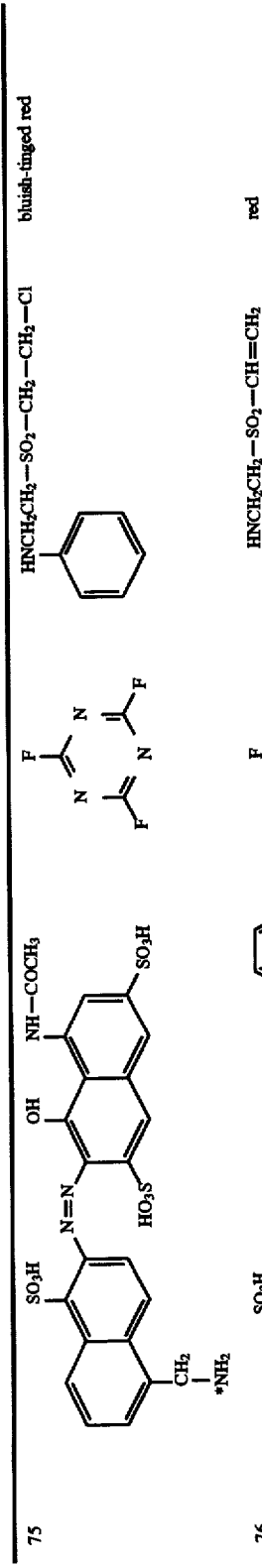 | | HNCH$_2$CH$_2$—SO$_2$—CH$_2$—CH$_2$—Cl | bluish-tinged red |
| 76 | 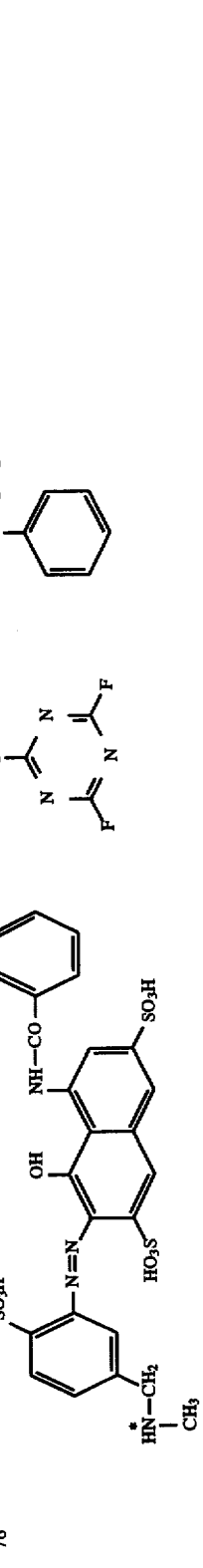 | | HNCH$_2$CH$_2$—SO$_2$—CH=CH$_2$ | red |
| 77 | 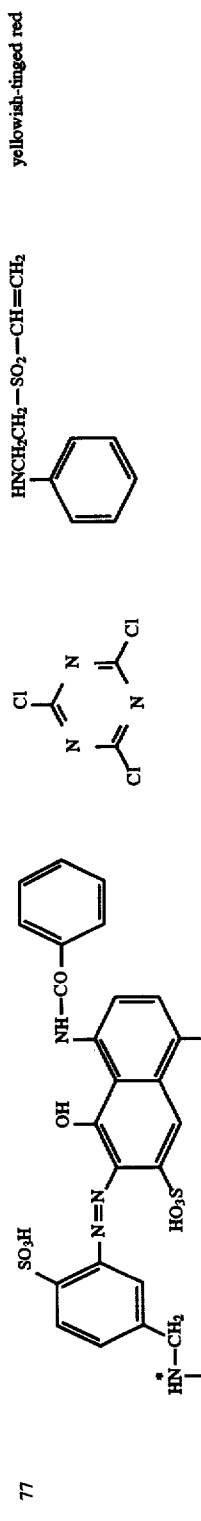 | | HNCH$_2$CH$_2$—SO$_2$—CH=CH$_2$ | yellowish-tinged red |
| No. | Diaminobenzenesulphonic acid | Trihalogenotriazine | Coupling component | Component of the formula (V) | Colour shade |
|---|---|---|---|---|---|
| 80 | 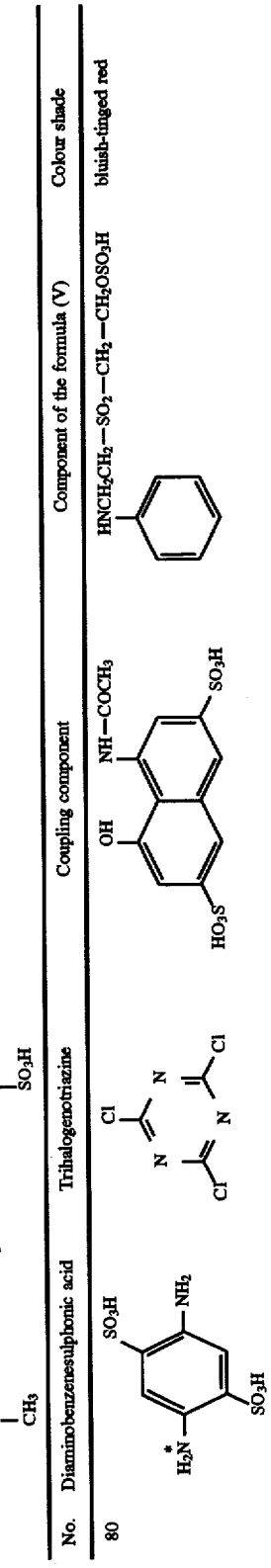 | | | HNCH$_2$CH$_2$—SO$_2$—CH$_2$—CH$_2$OSO$_3$H | bluish-tinged red |

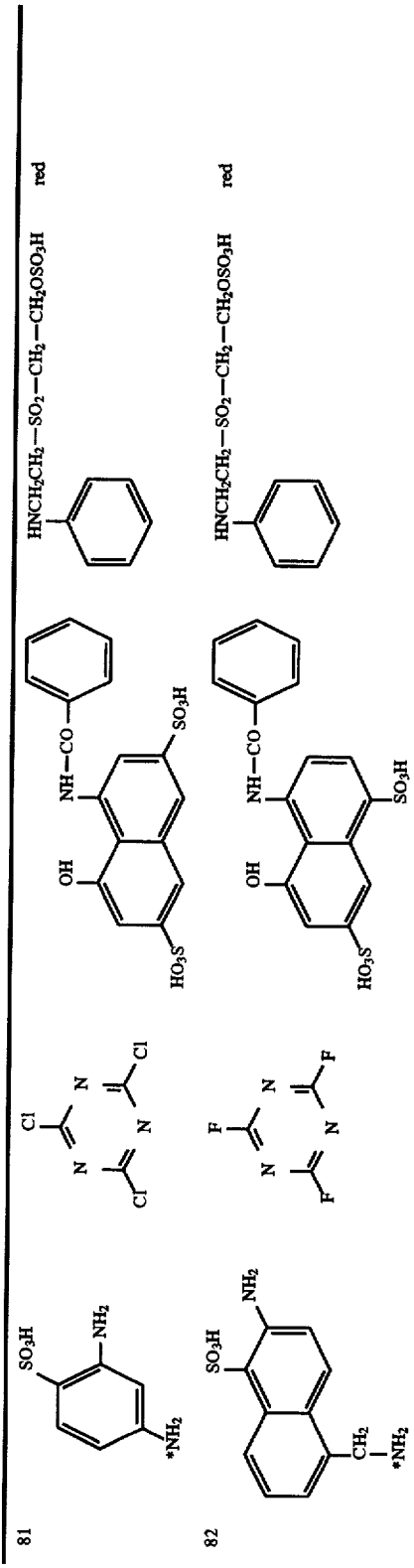
Wherein * identifies the atom bonded to the triazine ring.

EXAMPLE 83

36.7 g of the aminodisazo compound, prepared by the known route, of the formula

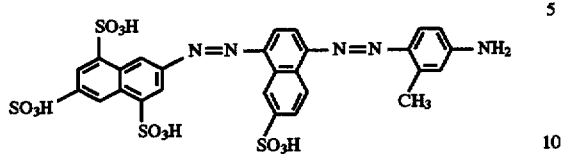

are dissolved in 400 ml of water at a pm of 6.0. 0.15 mol of reactive component (VIb) prepared in Example 1A is added and the mixture is subjected to a condensation reaction at 20° C. and pH 8 for about 8 hours.

The resulting dyestuff of the formula

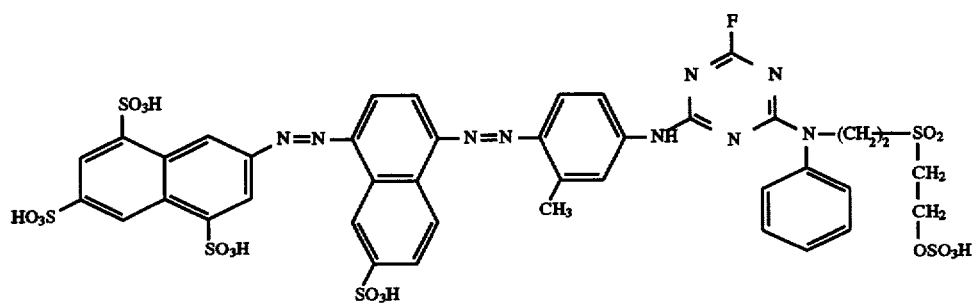

is salted out with sodium chloride, filtered off with suction and, after buffering at pH 6, dried in vacuo at 45° C. It dyes cotton in brown shades with a good yield by the processes known for reactive dyestuffs.

EXAMPLE 83a

If the compound of the formula

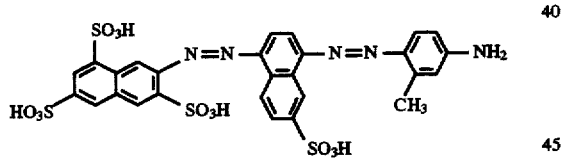

is employed instead of the aminodisazo compound of Example 83, a dyestuff of the formula

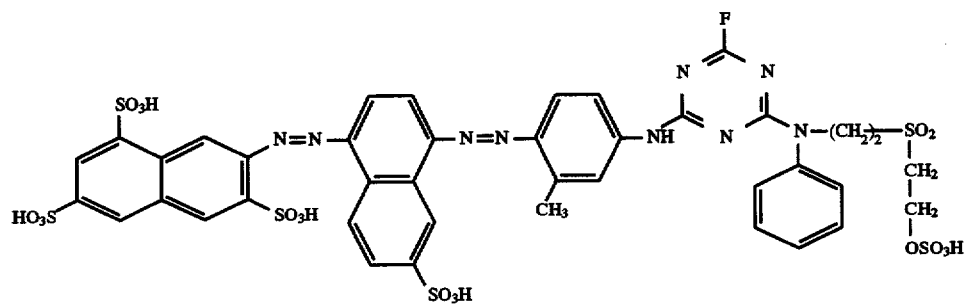

which likewise dyes cotton in brown shades with a good yield, is obtained.

Further brown reactive dyestuffs are obtained by condensation of the following components.

| No. | Aminodisazo compound | Trihalogenotriazine | Component of the formula (V) | Colour shade |
|---|---|---|---|---|
| 84 | (naphthalene bis-azo structure with CH₃, NH₂, SO₃H substituents) | F-triazine-F,F | HNCH₂CH₂—SO₂—CH₂—CH₂OSO₃H + phenyl | brown |
| 85 | (naphthalene bis-azo structure with CH₃, NH₂, SO₃H substituents) | F-triazine-F,F | HNCH₂CH₂—SO₂—CH₂—CH₂OSO₃H + phenyl | brown |
| 86 | (naphthalene bis-azo structure with NH₂, SO₃H substituents) | F-triazine-F,F | HNCH₂CH₂—SO₂—CH₂—CH₂OSO₃H + phenyl | brown |
| 87 | (naphthalene bis-azo structure with CH₃, CH₃, NH₂, SO₃H substituents) | F-triazine-F,F | HNCH₂CH₂—SO₂—CH₂—CH₂OSO₃H + phenyl | orange-brown |

EXAMPLE 88

50.3 g of the aminoazo compound (0.1 mol) of the formula

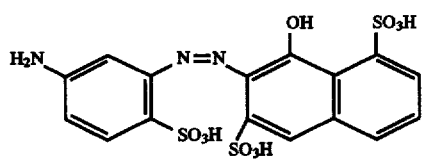

are dissolved in 400 ml of water under neutral conditions. 0.15 mol of the condensation solution prepared in Example 1A is added. A pH of 7–8 is maintained for 8 hours with $Na_2CO_2$ solution. The dyestuff of the formula

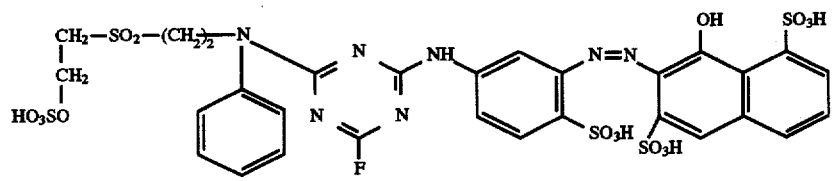

is then isolated by salting out and filtration with suction. After gentle drying, a powder which dyes cotton in scarlet shades with a good yield by the customary methods is obtained.

Further reactive dyestuffs based on aminoazonaphthol compounds are obtained by condensation of the following components.

| No. | Aminoazonaphthol component | Trihalogenotriazine | Component of the formula (V) | Colour shade |
|---|---|---|---|---|
| 89 | naphthol-OH with N=N to aminobenzene-SO₃H, SO₃H | 2,4,6-trifluorotriazine | HNCH₂CH₂—SO₂—CH₂—CH₂OSO₃H phenyl | orange |
| 90 | naphthol-OH with N=N to aminobenzene-SO₃H, SO₃H | 2,4,6-trifluorotriazine | HNCH₂CH₂—SO₂—CH₂—CH₂OSO₃H phenyl | orange |
| 91 | naphthol-OH, SO₃H with N=N to aminobenzene-SO₃H, SO₃H | 2,4,6-trifluorotriazine | HNCH₂CH₂—SO₂—CH₂—CH₂OSO₃H phenyl | yellowish-tinged red |
| 92 | phenylamino-naphthol-OH with N=N to methyl-aminobenzene-SO₃H, HO₃S | 2,4,6-trifluorotriazine | HNCH₂CH₂—SO₂—CH₂—CH₂OSO₃H phenyl | yellowish-tinged red |

EXAMPLE 93

35.2 g of the known compound (0.05 mol)

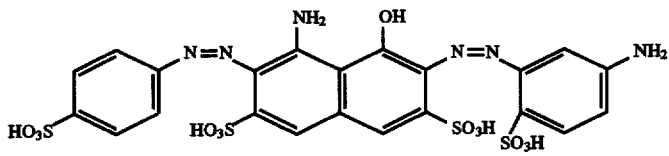

are dissolved in 350 ml of water, and the pH of the solution is brought to 7.0. 0.06 mol of the condensation solution prepared in Example 1A is added to this solution. The reaction is carried out at pB 7–8 and at 20°–25° C. for 6–7 hours.

When the condensation has ended, the dyestuff is isolated, after buffering to pH 6, either directly by spray drying or by salting out, filtration with suction and vacuum drying at 40° C. The dyestuff has the formula

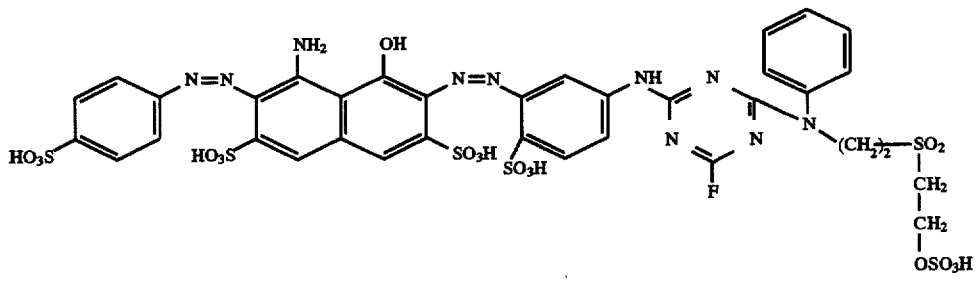

and dyes cotton in navy blue shades with a very good yield by the dyeing techniques customary for reactive dyestuffs.

Further similar reactive dyestuffs which dye cellulose fibres navy blue to black are obtained when the aminodisazo components of the general formula

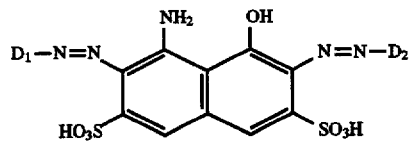

shown in the following list are subjected to a condensation reaction with the trihalogenotriazines and compounds of the formula (V).

| | Aminodisazo component | | Trihalogeno- | Component of | Colour |
|---|---|---|---|---|---|
| No. | D₁ | D₂ | triazine | the formula (V) | shade |
| 94 | 4-HO₃S-C₆H₄- | 4-SO₃H, 3-(-), 6-NH₂ phenyl | 2,4,6-trifluoro-1,3,5-triazine | HN(C₆H₅)—CH₂—CH₂—SO₂—CH₂—CH₂—OSO₃H | navy |
| 95 | 4-H₂N—O₂S-C₆H₄- | 4-SO₃H, 3-(-), 6-NH₂ phenyl | 2,4,6-trifluoro-1,3,5-triazine | HN(C₆H₅)—CH₂—CH₂—SO₂—CH₂—CH₂—OSO₃H | navy |
| 96 | 2,5-disulfo phenyl | 4-SO₃H, 3-(-), 6-NH₂ phenyl | 2,4,6-trifluoro-1,3,5-triazine | HN(C₆H₅)—CH₂—CH₂—SO₂—CH₂—CH₂—OSO₃H | navy |
| 97 | 2-SO₃H, 5-NH₂ phenyl | 3-SO₃H phenyl | 2,4,6-trifluoro-1,3,5-triazine | HN(C₆H₅)—CH₂—CH₂—SO₂—CH₂—CH₂—OSO₃H | navy |
| 98 | 4-HO₃S-C₆H₄- | 2,5-disulfo-4-NH₂ phenyl | 2,4,6-trifluoro-1,3,5-triazine | HNCH₂CH₂—SO₂—CH₂—CH₂—OSO₃H (with C₆H₅) | black |
| 99 | 2,4-disulfo phenyl | 4-SO₃H, 3-(-), 6-NH₂ phenyl | 2,4,6-trichloro-1,3,5-triazine | HNCH₂CH₂—SO₂—CH₂—CH₂—OSO₃H (with C₆H₅) | navy |
| 100 | 1-SO₃H, 5-SO₃H naphthyl | 4-SO₃H, 3-(-), 6-NH₂ phenyl | 2,4,6-trifluoro-1,3,5-triazine | HNCH₂CH₂—SO₂—CH₂—CH₂—OSO₃H (with C₆H₅) | black |

EXAMPLE 101

50 mmol of the copper complex compound of the formula

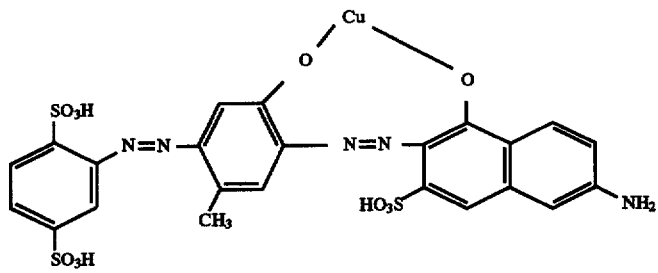

are dissolved in 600 ml of water at pH 6.5. 60 mmol of the compound, prepared in Example 1A, of the formula

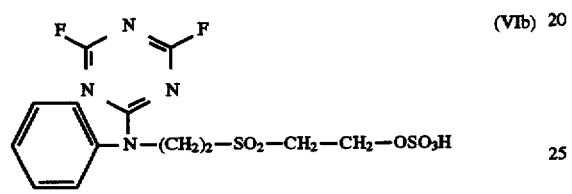

(VIb)

are added to the dyestuff solution and the mixture is subjected to a condensation reaction at 20°–25° C. and at pH 6.5–7. When the reaction has ended, the dyestuff of the formula

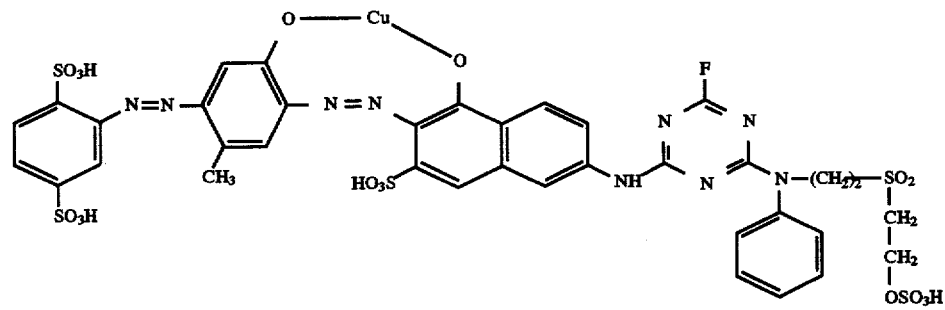

is salted out, isolated and, after buffering to pH 6, dried in vacuo at 45° C.

The product dyes cellulose fibres in navy blue shades with a very good fixing yield by the dyeing techniques customary for reactive dyestuffs.

Further reactive dyestuffs which dye cotton with a very good yield by the customary dyeing techniques are obtained when the known copper complex compounds shown in the following list are subjected to a condensation reaction with the trihalogenotriazines and the components of the formula (V) by the procedures described in Example 101.

| No. | Copper complex compound | Trihalogeno-triazine | Component of the formula (V) | Colour shade |
|---|---|---|---|---|
| 102 | | trifluorotriazine | HN—(CH₂)₂—SO₂—CH₂—CH₂OSO₃H with phenyl | navy blue |
| 103 | | trifluorotriazine | HN—(CH₂)₂—SO₂—CH₂—CH₂OSO₃H with phenyl | navy blue |
| 104 | | trifluorotriazine | HN—(CH₂)₂—SO₂—CH₂—CH₂OSO₃H with phenyl | reddish-tinged navy blue |
| 105 | | trifluorotriazine | HN—(CH₂)₂—SO₂—CH₂—CH₂OSO₃H with phenyl | navy blue |

-continued

| No. | Copper complex compound | Trihalogeno-triazine | Component of the formula (V) | Colour shade |
|---|---|---|---|---|
| 106 | (copper complex structure) | (trifluorotriazine) | HN—(CH$_2$)$_2$—SO$_2$—CH$_2$—CH$_2$OSO$_3$H —phenyl | navy blue |
| 107 | (copper complex structure) | (difluorotriazine) | HN—(CH$_2$)$_2$—SO$_2$—CH$_2$—CH$_2$OSO$_3$H —phenyl | dark blue |
| 108 | (copper complex structure) | (difluorotriazine) | HN—(CH$_2$)$_2$—SO$_2$—CH$_2$—CH$_2$OSO$_3$H —phenyl | green |
| 109 | (copper complex structure) | (difluorotriazine) | HN—(CH$_2$)$_2$—SO$_2$—CH$_2$—CH$_2$OSO$_3$H —phenyl | red-violet |

| No. | Copper complex compound | Trihalogeno-triazine | Component of the formula (V) | Colour shade |
|---|---|---|---|---|
| 110 | Cu complex azo dye with NH₂, SO₃H, HO₃S substituents | 2,4,6-trichlorotriazine | HN—(CH₂)₂—SO₂—CH₂—CH₂OSO₃H, phenyl | navy blue |
| 111 | Cu complex azo dye with NH₂, SO₃H, SO₃H substituents | 2,4,6-trifluorotriazine | HN—(CH₂)₂—SO₂—CH₂—CH₂OSO₃H, phenyl | navy blue |
| 112 | Cu complex azo dye with NH₂, SO₃H, HO₃S substituents | 2,4,6-trifluorotriazine | HN—(CH₂)₂—SO₂—CH₂—CH₂OSO₃H, phenyl | blue-violet |

Further interesting dyestuffs, for example from the ortho-disazo metal complex series, are:

EXAMPLE 113

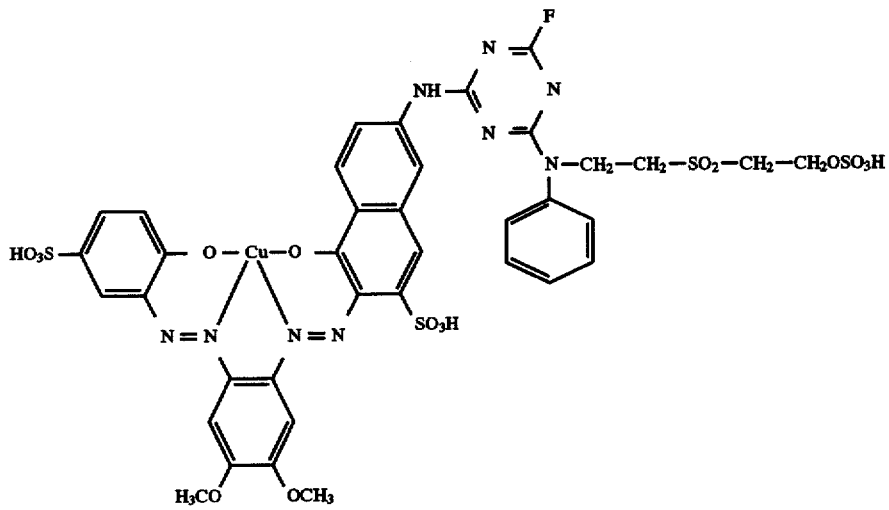

which dyes cotton in olive colour shades, or, from the ortho-aminoazo metal complex series, for example the dyestuff of the formula

EXAMPLE 114

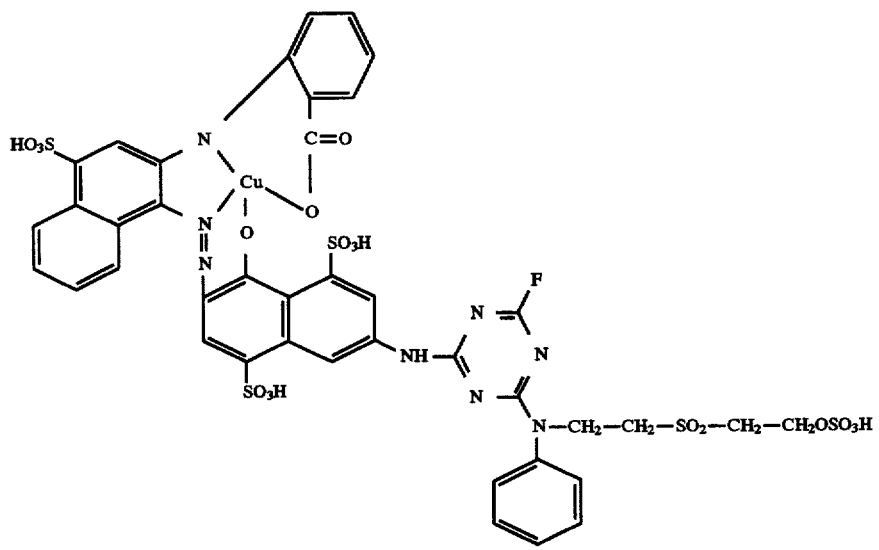

which dyes cotton in green shades.

EXAMPLE 115

3 mol of 2-phenylaminoethanol of the formula

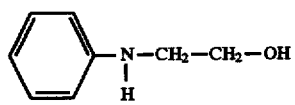

were added dropwise to 1400 parts of sulphuric acid (100% strength) at 20°–30° C. in the course of 1 hour. The mixture was subsequently stirred for 2 hours. The melt thus obtained was discharged onto ice at 0° C. and subsequently stirred at 0°–5° C. for 1 hour. The product which had precipitated was isolated. About 1500 parts of the ester were obtained as a pale beige paste, to which the following formula:

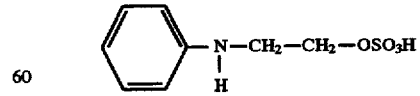

is attributed. The entire paste was suspended in 2500 parts of water and the pH was brought to 7 with 50% strength potassium hydroxide solution. At 60° C., in the course of 20 minutes, 3 mol of mercaptoethanol and then 3 mol of potassium hydroxide (50% strength solution) were added dropwise. The mixture was boiled under reflux for 8 hours. The resulting oil was separated off. The aqueous phase was extracted by shaking with ether. After the ether had been distilled off, the product was combined. 460 parts of the thio compound were obtained as an oil having the formula

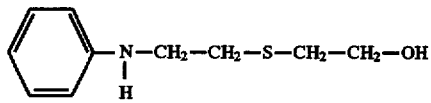

¹H-NMR (D₆-DMSO)
δ=2.58–2.75 ppm (6H, m)
δ=3.22 ppm (2H, t)
δ=4.80 ppm (1H, s)
δ=6.50–6.61 ppm (3H, m)
δ=7.05 ppm (2H, d)

EXAMPLE 116

460 parts of the thioether were taken up in 1000 parts of acetone and 1000 parts of water. 2.6 mol of acetic anhydride were added dropwise in the course of 1 hour. The temperature rose to about 45° C. The mixture was subsequently stirred for 2 hours, and 14 g of sodium tungstate were added. 4.9 mol of 35% strength $H_2O_2$ were then added dropwise in the course of 1 hour. The temperature rose to 50°–55° C. The acetone was distilled off and the solution which remained was cooled to 10° C. The product formed precipitated and was isolated. This gave 1020 parts of a paste, to which the following formula is attributed:

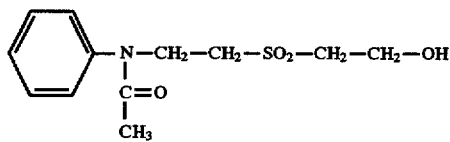

¹H-NMR (D₆-DMSO)
δ=1.77 ppm (1H, s)
δ=3.21–3.38 ppm (4H, m)
δ=3.76 ppm (2H, q)
δ=4.05 ppm (2H, t)
δ=5.10 ppm (1H, t)
δ=7.38–7.55 ppm (5H, m)

EXAMPLE 117

1020 parts of the paste were suspended in 1500 parts of water, and 300 parts of 30% strength hydrochloric acid solution were added. The mixture was boiled under reflux for 3 hours. The solution was cooled to 10° C. and brought to pH 9 with sodium hydroxide solution. The resulting oil was separated off. The aqueous phase was extracted by shaking with ethyl acetate. After the ethyl acetate had been distilled off, the fractions of the resultant oil of the formula

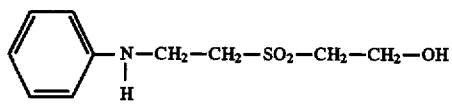

were combined and dried. This gave 450 parts of the sulphone as an oil.

¹H-NMR (D₆-DMSO)
δ=3.23–3.55 ppm (6H, m)
δ=3.85 ppm (2H, t)
δ=5.30 ppm (1H, s)
δ=5.78 ppm (1H, t)
δ=6.60 ppm (3H, d)
δ=7.10 ppm (2H, t)

EXAMPLE 118

450 parts of the above substance were added dropwise to parts of sulphuric acid at 20°–30° C. in the course of 1 hour. After 8 hours, the melt was discharged onto ice and the mixture was subsequently stirred at 0°–5° C. for about 1 hour. The pale beige crystalline product was isolated. 910 parts of a paste were obtained. The compound formed has the following formula:

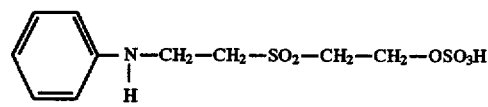

The yield is 45–50% over all steps (Example 115 to 118).
¹H-NMR (D₆-DMSO)
δ=3.43 ppm (2H, t)
δ=3.50 ppm (2H, t)
δ=3.60 ppm (2H, t)
δ=4.11 ppm (2H, t)
δ=7.00 ppm (3H, d, d)
δ=7.30 ppm (2H, t)
δ=8.98 ppm (2H, s)

EXAMPLE 119

A) 0.15 mol of the compound of the formula

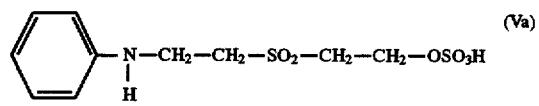

(Va)

was stirred into 100 parts of water and 100 parts of ice to give a neutral solution. 0.165 mol of 2,4,6-trifluoro-1,3,5-triazine was added dropwise over 10 minutes at 0° C. and pH 4–4.5. About 250 parts of an aqueous condensation solution having the following structure were obtained:

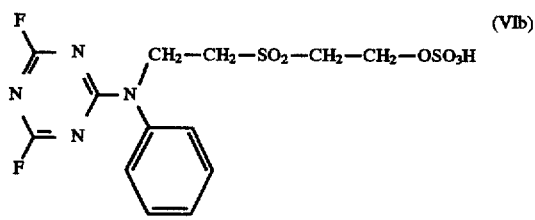

(VIb)

B) 0.1 mol of 1-amino-8-hydroxy-3,6-naphthalenedisulphonic acid was suspended in 150 parts of water and the suspension was converted to a neutral solution with lithium hydroxide solution. 0.1 mol of the above condensation solution was added. A pH of 4–4.5 was maintained at 20° C. using lithium carbonate. The reaction was over after 8 hours. A solution was present.

C) 0.1 mol of 1-sulpho-2-naphthylamine-6-β-sulphatoethyl sulphone were diazotised in a suitable manner and coupled at pH 7.5–8.5 with the H acid condensation product. The dyestuff was salted out by adding potassium chloride and isolated. After drying, about 35 g of a salt-containing dyestuff coupler were obtained, to which the structure

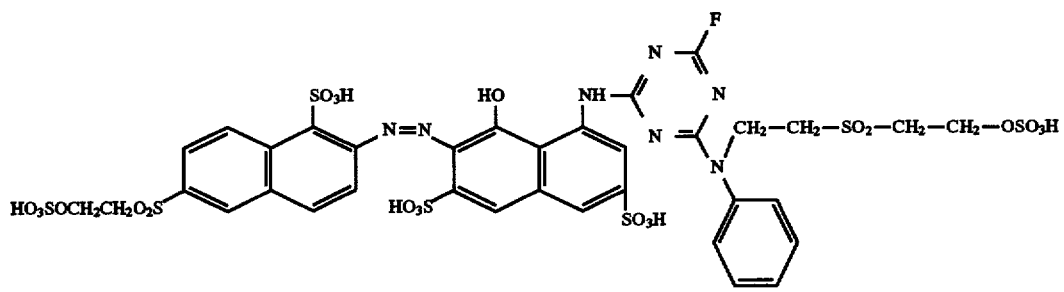

($\lambda_{max}$=516 and 538 nm ($H_2O$)) is attributed and which dyes cotton in red colour shades by the dying or printing processes customary for reactive dyestuffs.

EXAMPLE 120

0.1 mol of 4-(β-sulphatoethylsulphonyl)analine was suspended in 200 parts of water and 100 parts of ice at 0° C. 28 parts of concentrated hydrochloric acid were added. A solution of 7 parts of sodium nitrite in 70 parts of water was added dropwise over 15 minutes. After stirring for a further 30 minutes the diazotisation was over. A pale yellow suspension was obtained. The excess nitrite was destroyed using amidosulphonic acid.

This suspension was then metered in over a period of 15–20 minutes to 0.1 mol of the H acid condensation product from Example 119B. Coupling was carried out at 20° C. and a pH of 7–8. The dyestuff was precipitated by addition of ethanol and isolated. After drying, about 40 g of a dyestuff powder were obtained to which the structure

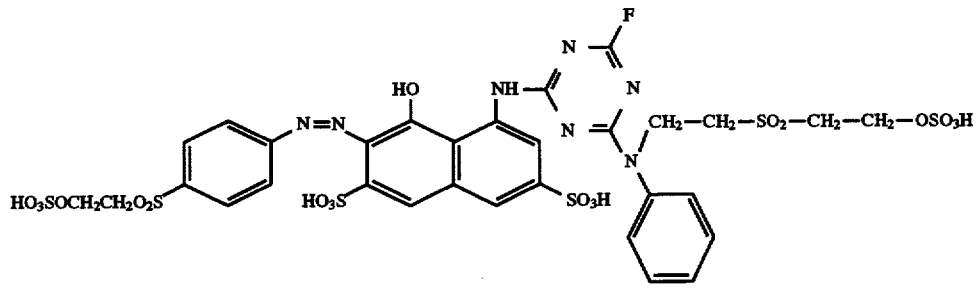

($\lambda_{max}$=517 nm ($H_2O$)) is attributed and which dyes cotton in red colour shades by the dyeing and printing processes customary for reactive dyestuffs.

Further red reactive dyestuffs are obtained by condensation of the following components.

| No. | Diazo component | 1-Amino-8-hydroxy-naphthalene-disulphonic acid | Trihalogeno-triazine | Component of the formula (V) | Colour shade | $\lambda_{max}$ (H$_2$O) |
|---|---|---|---|---|---|---|
| 121 | 3-aminophenyl-CH$_2$SO$_2$CH$_2$CH$_2$OSO$_3$H | H-acid (NH$_2$, OH, 2×SO$_3$H) | trifluoro-triazine | HN—CH$_2$—CH$_2$—SO$_2$—CH$_2$—CH$_2$—OSO$_3$H (anilino) | blueish-tinged red | |
| 122 | 4-amino-phenyl-SO$_2$CH$_2$CH$_2$OSO$_3$H | H-acid | trifluoro-triazine | HN—CH$_2$—CH$_2$—SO$_2$—CH$_2$—CH$_2$—OSO$_3$H (anilino) | red | |
| 123 | 2-amino-naphthyl-1-SO$_3$H, 6-SO$_2$CH$_2$CH$_2$OSO$_3$H | H-acid | trifluoro-triazine | HN—CH$_2$—CH$_2$—SO$_2$—CH$_2$—CH$_2$—OSO$_3$H (anilino) | red | |
| 124 | 2-amino-naphthyl-1-SO$_3$H, 6-SO$_2$CH$_2$CH$_2$OSO$_3$H | H-acid | 2,4-dichloro-6-fluoro-triazine | HN—CH$_2$—CH$_2$—SO$_2$—CH$_2$—CH$_2$—OSO$_3$H (anilino) | red | |
| 125 | 4-aminophenyl-CH$_2$SO$_2$CH$_2$CH$_2$OSO$_3$H | H-acid | trifluoro-triazine | HN—CH$_2$—CH$_2$—SO$_2$—CH$_2$—CH$_2$—OSO$_3$H (anilino) | blueish-tinged red | 512 |
| 126 | 4-aminophenyl-CH$_2$SO$_2$CH$_2$CH$_2$OSO$_3$H | H-acid | 2,4-dichloro-6-fluoro-triazine | HN—CH$_2$—CH$_2$—SO$_2$—CH$_2$—CH$_2$—OSO$_3$H (anilino) | blueish-tinged red | 534 |

-continued

| No. | Diazo component | 1-Amino-8-hydroxy-naphthalene-disulphonic acid | Trihalogenotriazine | Component of the formula (V) | Colour shade | $\lambda_{max}$ ($H_2O$) |
|---|---|---|---|---|---|---|
| 127 | 2-amino-6-(SO$_2$CH$_2$CH$_2$OSO$_3$H)-1-SO$_3$H naphthalene | 1-NH$_2$, 8-OH, 3,6-di-SO$_3$H naphthalene | 2,4,6-trichloro-triazine | HN—C$_6$H$_5$ / —SO$_2$—CH$_2$—CH$_2$—OSO$_3$H | red | 518, 540 |
| 128 | 3-amino-(SO$_2$CH$_2$CH$_2$OSO$_3$H)-aniline | 1-NH$_2$, 8-OH, 4,6-di-SO$_3$H naphthalene | 2,4,6-trichloro-triazine | HN—C$_6$H$_5$ / —SO$_2$—CH$_2$—CH$_2$—OSO$_3$H | bluish-tinged red | — |
| 129 | 4-amino-(CH$_2$CH$_2$OSO$_3$H-sulphonyl)-aniline | 1-NH$_2$, 8-OH, 3,6-di-SO$_3$H naphthalene | 2,4,6-trifluoro-triazine | HN—(3-CH$_3$-C$_6$H$_4$) / —SO$_2$—CH$_2$—CH$_2$—OSO$_3$H | bluish-tinged red | 522, 544 |
| 130 | 4-amino-(CH$_2$CH$_2$OSO$_3$H-sulphonyl)-aniline | 1-NH$_2$, 8-OH, 3,6-di-SO$_3$H naphthalene | 2,4,6-trichloro-triazine | HN—(3-CH$_3$-C$_6$H$_4$) / —SO$_2$—CH$_2$—CH$_2$—OSO$_3$H | bluish-tinged red | — |
| 131 | 2-amino-6-(SO$_2$CH$_2$CH$_2$OSO$_3$H)-1-SO$_3$H naphthalene | 1-NH$_2$, 8-OH, 3,6-di-SO$_3$H naphthalene | 2,4,6-trifluoro-triazine | HN—(3-CH$_3$-C$_6$H$_4$) / —SO$_2$—CH$_2$—CH$_2$—OSO$_3$H | red | 519, 538 |
| 132 | 2-amino-6-(SO$_2$CH$_2$CH$_2$OSO$_3$H)-1-SO$_3$H naphthalene | 1-NH$_2$, 8-OH, 3,6-di-SO$_3$H naphthalene | 2,4,6-trichloro-triazine | HN—(3-CH$_3$-C$_6$H$_4$) / —SO$_2$—CH$_2$—CH$_2$—OSO$_3$H | red | 519, 540 |

-continued

| No. | Diazo component | 1-Amino-8-hydroxy-naphthalene-disulphonic acid | Trihalogeno-triazine | Component of the formula (V) | Colour shade | $\lambda_{max}$ ($H_2O$) |
|---|---|---|---|---|---|---|
| 133 | 4-($\beta$-sulphatoethylsulphonyl)aniline (SO$_2$-CH$_2$-CH$_2$-OSO$_3$H on para, NH$_2$) | 1-amino-8-hydroxy-3,6-disulpho (NH$_2$, OH, SO$_3$H, HO$_3$S) | 2,4,6-trichlorotriazine | HN—C$_6$H$_5$, with HN—CH$_2$—CH$_2$—SO$_2$—CH$_2$—CH$_2$—OSO$_3$H | red | |
| 134 | 3-amino-($\beta$-methylsulphonylethylsulphate) (NH$_2$, CH$_3$SO$_2$CH$_2$CH$_2$OSO$_3$H) | 1-amino-8-hydroxy-3,6-disulpho | 2,4,6-trifluorotriazine | HN—C$_6$H$_5$, HN—CH$_2$—CH$_2$—SO$_2$—CH$_2$—CH$_2$—OSO$_3$H | blueish-tinged red | |
| 135 | 3-($\beta$-sulphatoethylsulphonyl)aniline (NH$_2$, SO$_2$CH$_2$CH$_2$OSO$_3$H) | 1-amino-8-hydroxy-3,6-disulpho | 2,4,6-trifluorotriazine | HN—C$_6$H$_5$, HN—CH$_2$—CH$_2$—SO$_2$—CH$_2$—CH$_2$—OSO$_3$H | blueish-tinged red | |
| 136 | 4-($\beta$-sulphatoethylsulphonylmethyl)aniline (NH$_2$, SO$_2$CH$_2$CH$_2$OSO$_3$H) | 4-aminophenyl-NH-CO-naphthol-SO$_3$H, HO$_3$S, OH | 2,4,6-trifluorotriazine | HN—C$_6$H$_5$, HN—CH$_2$—CH$_2$—SO$_2$—CH$_2$—CH$_2$—OSO$_3$H | blueish-tinged red | |
| 137 | 4-($\beta$-sulphatoethylsulphonylmethyl)aniline (NH$_2$, SO$_2$CH$_2$CH$_2$OSO$_3$H) | 4-aminophenyl-NH-CO-naphthol-SO$_3$H, OH, HO$_3$S | 2,4,6-trichlorotriazine | HN—C$_6$H$_5$, HN—CH$_2$—CH$_2$—SO$_2$—CH$_2$—CH$_2$—OSO$_3$H | blueish-tinged red | |

EXAMPLE 138

0.1 mol of the monoazo compound with the formula

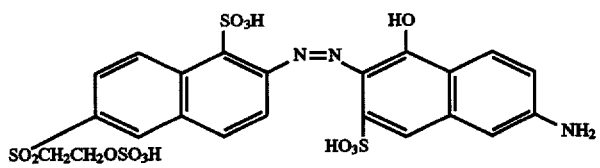

was dissolved in about 500 parts of water under neutral conditions. 0.15 mol of the condensation solution prepared in Example 119 was added. A pH of 7–8 was maintained at 20° C. using sodium carbontate solution. After 2 hours the reaction was finished to a very large extent. The dyestuff was salted out by adding potassium chloride, isolated and dried. About 82 g of a salt-containing dyestuff powder were obtained to which the structure

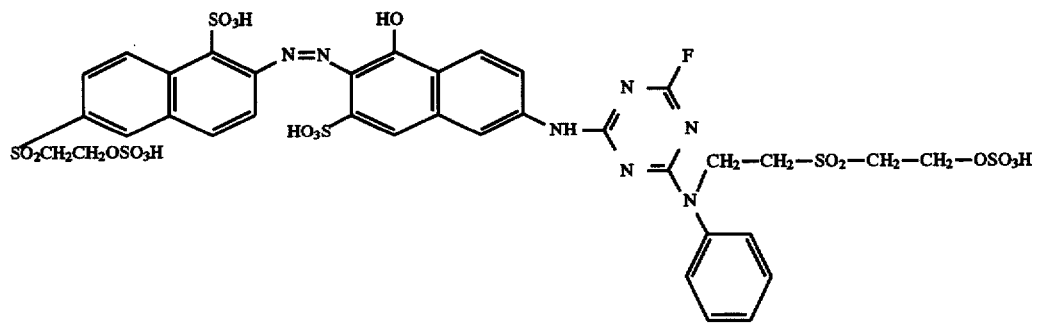

($\lambda_{max}$=492 nm (H$_2$O)) is attributed and which dyes cotton in orange colour shades by the dying or printing processes customary for reactive dyestuffs.

EXAMPLE 139

0.1 mol of 4-aminophenyl β-sulphatoethyl sulphone was dissolved in 100 parts of water and 100 parts of ice under neutral conditions. 28 parts of concentrated hydrochloric acid were added. A solution of 7 parts of sodium nitride in 70 parts of water was added dropwise over 15 minutes. After stirring for a further 30 minutes the diazotisation was finished. The excess nitrite was destroyed using amidosulphonic acid.

0.12 mol of 7-amino-4-hydroxy-2-naphthalenesulphonic acid was suspended in 300 parts of water and dissolved at pH=6–6.5 using 10% strength lithium hydroxide solution. 0.18 mol of the condensation solution prepared in Example 119A was added. A pH of 4–5 was maintained at 20° C. using sodium carbonate solution. After 2 hours the condensation was finished. 900 parts of a solution were obtained. The product was salted out with 180 parts of potassium chloride and isolated. About 220 parts of a grey paste were obtained. The paste was dissolved in 600 parts of water. The above diazotisation mixture was added dropwise and at the same time a pH of 6–6.5 was maintained by addition of NaHCO$_3$. The pH was then adjusted to 7.5–8 using sodium carbonate solution. The solution was stirred overnight.

The dyestuff was salted out by adding sodium chloride and isolated. After drying, about 105 g of a salt-containing dyestuff powder were obtained to which the structure

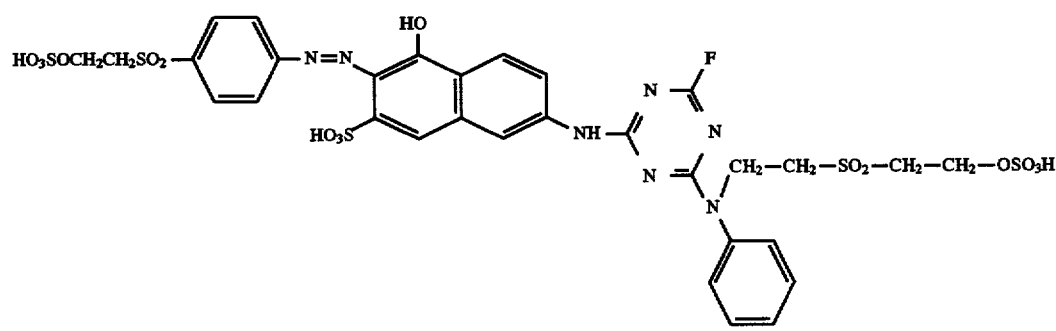

is attributed and which dyes cotton in scarlet shades by the dying or printing processes customary for reactive dyestuffs.

Further reactive dyestuffs are obtained by condensation of the following components in analogy to Example 138 or 139.

| No. | Azo component | Component of the formula (V) | Halogeno-triazine | Colour shade |
|---|---|---|---|---|
| 140 | naphthalene with SO₃H, N=N, OH, NH₂, SO₂CH₂CH₂OSO₃H substituents | HNCH₂CH₂—SO₂—CH₂—CH₂OSO₃H—phenyl | dichlorotriazine (Cl, N, N, N, Cl) | orange 492 nm |
| 141 | naphthalene with OH, N=N-phenyl-SO₂CH₂CH₂OSO₃H, HO₃S, NH₂ | HNCH₂CH₂—SO₂—CH₂—CH₂OSO₃H—phenyl | difluorotriazine (F, N, N, N, F) | orange |
| 142 | HO₃SOCH₂CH₂O₂S-phenyl-N=N-naphthalene(OH, HO₃S, NH₂) | HNCH₂CH₂—SO₂—CH₂—CH₂OSO₃H—phenyl | difluorotriazine | orange |
| 143 | HO₃SOCH₂CH₂O₂S-phenyl-N=N-naphthalene(OH, HO₃S, NH₂) | HNCH₂CH₂—SO₂—CH₂—CH₂OSO₃H—phenyl | difluorotriazine | orange |
| 144 | HO₃SOCH₂CH₂O₂S-phenyl-N=N-phenyl(SO₃H)-N=N-naphthalene(OH, HO₃S, NH₂) | HNCH₂CH₂—SO₂CH₂CH₂OSO₃H—phenyl | difluorotriazine | yellowish-tinged red λ$_{max}$ = 514 nm |
| 145 | HO₃SOCH₂CH₂SO₂-phenyl-N=N-phenyl(SO₃H)-N=N-naphthalene(OH, HO₃S, NH₂) | HNCH₂CH₂—SO₂CH₂CH₂OSO₃H—phenyl | dichlorotriazine | yellowish-tinged red λ$_{max}$ = 514 nm |

-continued

| No. | Azo component | Component of the formula (V) | Halogeno-triazine | Colour shade |
|---|---|---|---|---|
| 146 | HO₃S—OH₂C—CH₂—O₂S—C₆H₄—N=N—[naphthalene with OH, HO₃S, NH₂] | HNCH₂CH₂—SO₂—CH₂CH₂OSO₃H—C₆H₅ | dichlorotriazine | yellowish-tinged red λ_max = 510 nm |
| 147 | [naphthalene with OH, HO₃S, NH₂]—N=N—C₆H₄—SO₂CH₂CH₂OSO₃H | HNCH₂CH₂—SO₂—CH₂—CH₂OSO₃H—C₆H₅ | dichlorotriazine | orange |
| 148 | SO₃H, [naphthalene-naphthalene with OH, HO₃S, NH₂, SO₂CH₂CH₂SO₃H]—N=N— | HNCH₂CH₂—SO₂—CH₂—CH₂OSO₃H—C₆H₅ | dichlorotriazine | scarlet |
| 149 | SO₃H, [naphthalene-naphthalene with OH, HO₃S, NH₂, SO₂—CH₂—CH₂OSO₃H]—N=N— | HNCH₂CH₂—SO₂—CH₂—CH₂OSO₃H—C₆H₅ | dichlorotriazine | orange λ_max = 494 nm |

EXAMPLE 150

35.2 g of the known compound (0.05 mol)

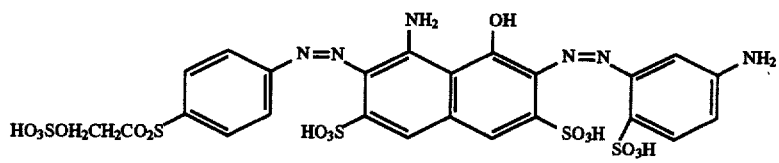

are dissolved in 350 ml of water and the pH of the solution is adjusted to 7.0. 0.06 mol of the condensation solution prepared in Example 119A is added to this solution. Reaction is carried out over 6–7 hours at pH 7–8 and 20°–25° C.

After condensation has been concluded the dyestuff is isolated, after buffering to pH 6, either directly by spray-drying or by salting out, filtering off with suction and vacuum-drying at 40° C. The dyestuff has the formula

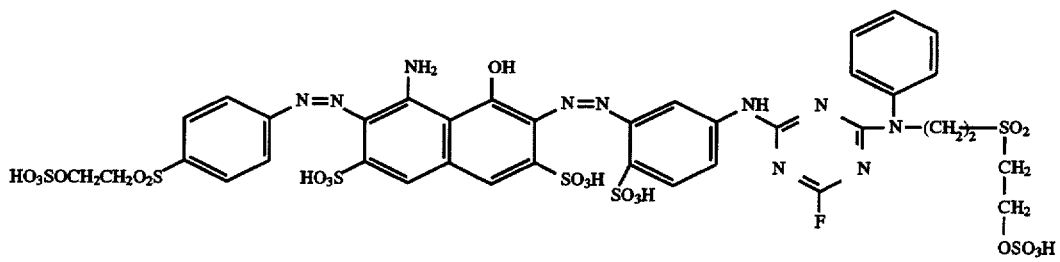

and dyes cotton in navy blue shades with a very good yield by the dyeing techniques customary for reactive dyestuffs.

Further similar reactive dyestuffs which dye cellulose fibres navy blue to black are obtained when the aminodisazo components of the general formula

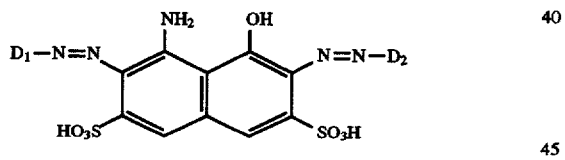

shown in the following list are subjected to a condensation reaction with the trihalogenotriazines and compounds of the formula (V).

| No. | Aminodisazo component D₁ | Aminodisazo component D₂ | Trihalogeno-triazine | Component of the formula (V) | Colour shade |
|---|---|---|---|---|---|
| 151 | 3-(SO₂CH₂CH₂OSO₃H)-phenyl (with CH₃) | 4-amino-2-methyl-benzenesulfonic acid | 2,4,6-trifluoro-triazine | HN—CH₂—CH₂—SO₂—CH₂—CH₂—OSO₃H (phenyl) | navy |
| 152 | 4-(HO₃SOCH₂CH₂SO₂)-tolyl | 4-amino-2-methyl-benzenesulfonic acid | 2,4-dichloro-6-fluoro-triazine | HN—CH₂—CH₂—SO₂—CH₂—CH₂—OSO₃H (phenyl) | navy |
| 153 | 3-(CH₂SO₂CH₂CH₂OSO₃H)-tolyl | 4-amino-2-methyl-benzenesulfonic acid | 2,4,6-trifluoro-triazine | HN—CH₂—CH₂—SO₂—CH₂—CH₂—OSO₃H (phenyl) | navy |
| 154 | 4-(HO₃SOCH₂CH₂SO₂)-tolyl | 4-amino-2-methyl-benzenesulfonic acid | 2,4,6-trifluoro-triazine | HN—CH₂—CH₂—SO₂—CH₂—CH₂—OSO₃H (phenyl) | navy |
| 155 | 4-(HO₃SOCH₂CH₂SO₂CH₂)-tolyl | 2-amino-4-methyl-benzene-1,5-disulfonic acid | 2,4,6-trifluoro-triazine | HNCH₂CH₂—SO₂—CH₂—CH₂OSO₃H (phenyl) | black |

-continued

| No. | Aminodisazo component D₁ | D₂ | Trihalogeno-triazine | Component of the formula (V) | Colour shade |
|---|---|---|---|---|---|
| 156 | 3-methylphenyl-SO₂CH₂OSO₃H | 4-SO₃H, 3-methyl-aniline | 2,4,6-trichloro-1,3,5-triazine | HNCH₂CH₂—SO₂—CH₂—CH₂OSO₃H (phenyl) | navy |
| 157 | 1-SO₃H, 3-methyl, 6-SO₂CH₂CH₂OSO₃H naphthalene | 4-SO₃H, 3-methyl-aniline | 2,4,6-trifluoro-1,3,5-triazine | HNCH₂CH₂—SO₂—CH₂—CH₂OSO₃H (phenyl) | black |

What is claimed is:

1. A compound of the general formula

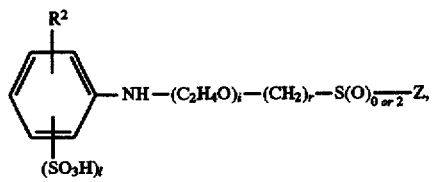

or a salt or its reaction products with protective groups, wherein $R^2$ denotes H, Cl, Br, $C_1$-$C_4$-alkoxy or COOH, Z denotes —$CH_2$—$CH_2$—$OSO_3H$, —$CH_2$—$CH_2$—$S_2O_3H$, —$CH_2$—$CH_2$—O—CO—$CH_3$, —$CH_2$—$CH_2$—$OPO_3H_2$ or —$CH_2$—$CH_2$—OH, j denotes 0 or 1, i denotes 0 or 1, and r denotes 2 or 3.

2. A method for the preparation of a compound of the general formula

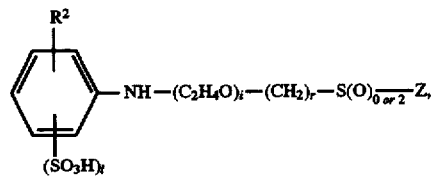

its salts and its reaction products with protective groups, wherein $R^2$ denotes H, $C_1$-$C_4$-alkyl, Cl, Br, $C_1$-$C_4$-alkoxy or COOH, Z denotes —CH=$CH_2$, —$CH_2$—$CH_2$—$OSO_3H$, —$CH_2$—$CH_2$—Cl, —$CH_2$—$CH_2$—Br, —$CH_2$—$CH_2$—$S_2O_3H$, —$CH_2$—$CH_2$—O—CO—$CH_3$, —$CH_2$—$CH_2$—$OPO_3H_2$ or —$CH_2$—$CH_2$—OH, j denotes 0 or 1, i denotes 0 or 1, and r denotes 2 or 3, which comprises sulphation of a compound of the formula

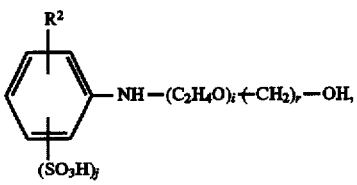

subsequent reaction with mercaptoethanol to give

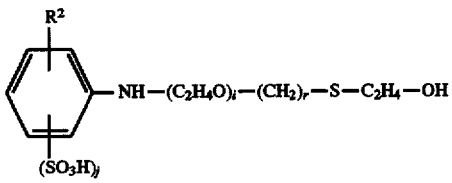

optionally blocking of the NH group with a protective group and oxidation to give

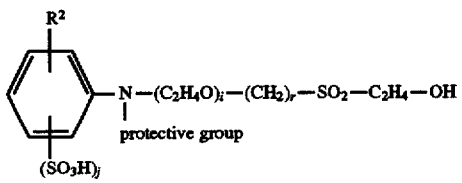

optionally splitting off of the protective group to give

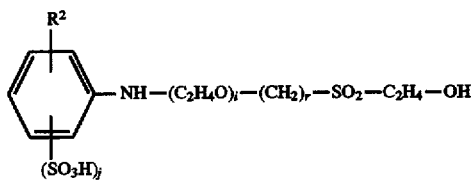

and optionally conversion of the radical $SO_2C_2H_4$—OH into the vinylsulphonyl group or conversion of the —$CH_2$—$CH_2$—OH group into the other detachable groups listed under Z.

* * * * *

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

It is certified that error appears in the above-identified patent and that said Letters Patent is hereby corrected as shown below:

Cols. 13-14, line 2    Delete formula (18)

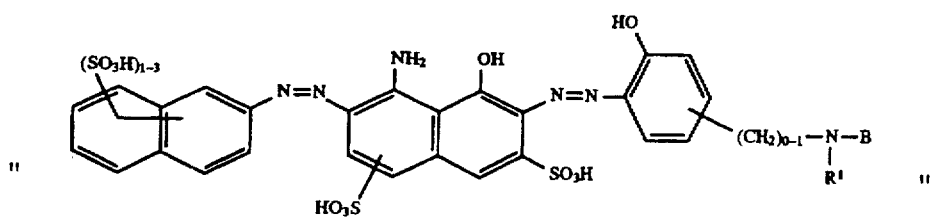

and substitute

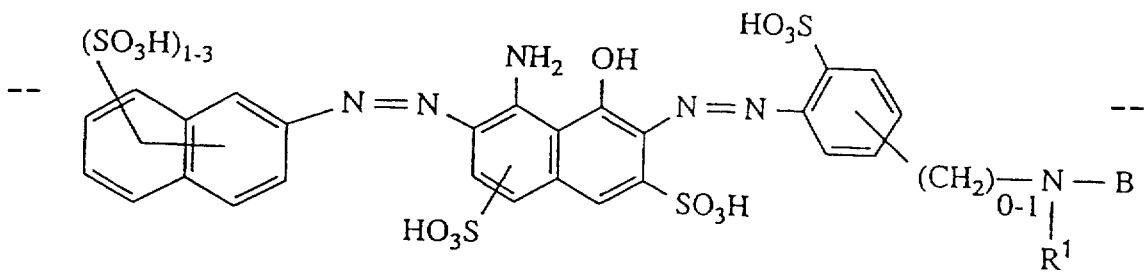

Col. 25, line 16    Delete " $C_3H_5$ , " and substitute
-- $C_2H_5$ , --

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

Page 2 of 9

It is certified that error appears in the above-identified patent and that said Letters Patent is hereby corrected as shown below:

Col. 42, No. 24    Under " Azo component " delete

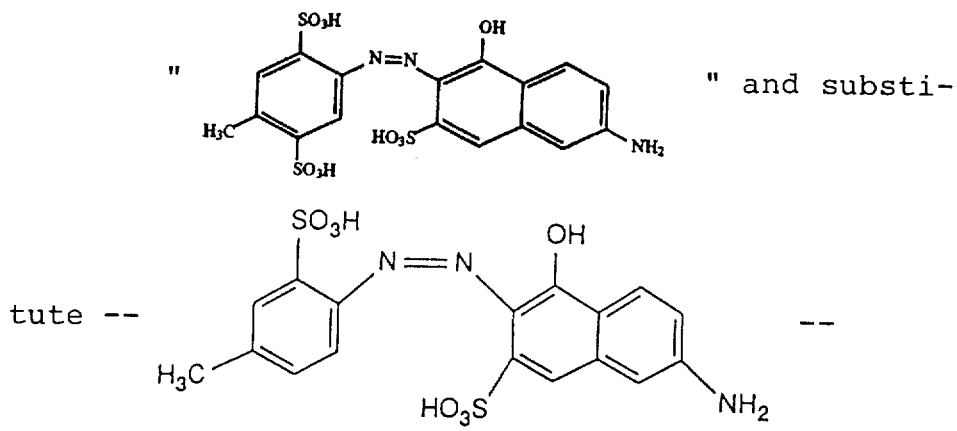

" and substitute --

Col. 49, No. 34    Under " Azo component " delete

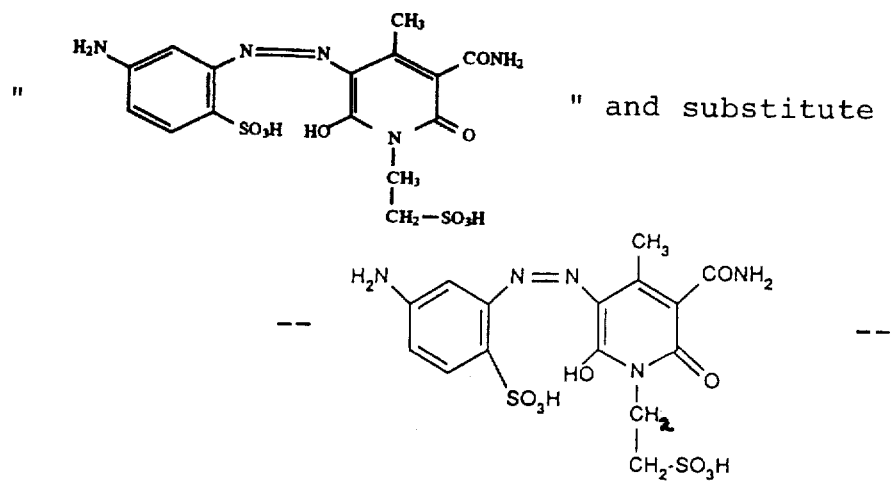

" and substitute --

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

Page 3 of 9

It is certified that error appears in the above-identified patent and that said Letters Patent is hereby corrected as shown below:

Col. 57, No. 48    Under " Aminophenylazopyrazolone " delete

"  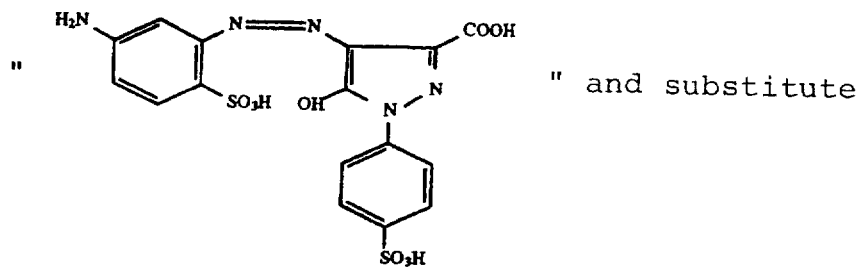  " and substitute

--  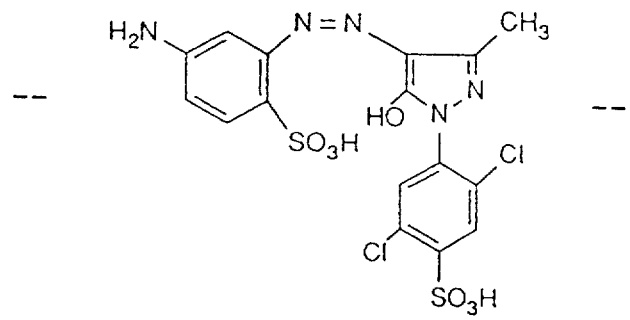  --

Col. 63, No. 61    Under " Azo component " delete

"  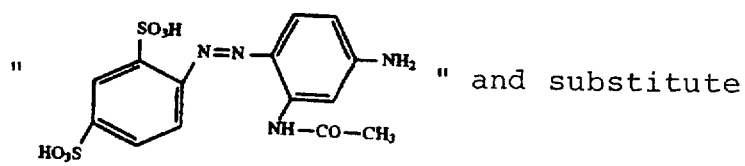  " and substitute

UNITED STATES PATENT AND TRADEMARK OFFICE
CERTIFICATE OF CORRECTION PATENT NO. : 5,686,642
DATED : November 11, 1997
INVENTOR(S) : Bootz, et al.

It is certified that error appears in the above-identified patent and that said Letters Patent is hereby corrected as shown below:

Col. 63, No. 61
Cont'd

-- 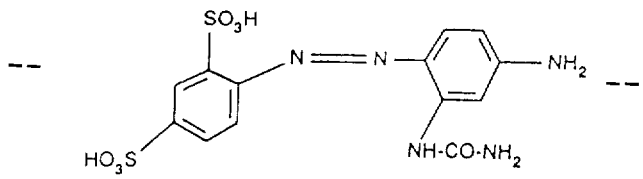 --

Col. 64, No. 62    Under " Azo component " and delete

" 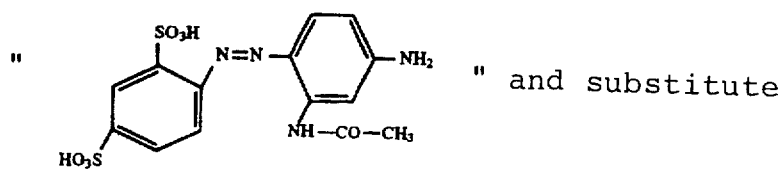 " and substitute

-- 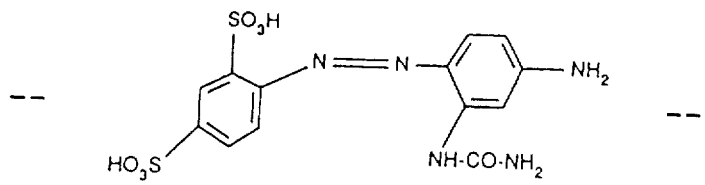 --

Col. 109, No. 142    Under " Azo component " delete

" 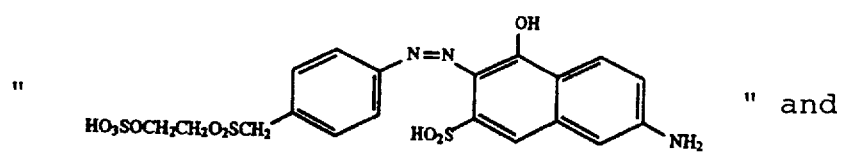 " and

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

Page 5 of 9

It is certified that error appears in the above-identified patent and that said Letters Patent is hereby corrected as shown below:

Col. 109, No. 142 Cont'd  substitute

-- 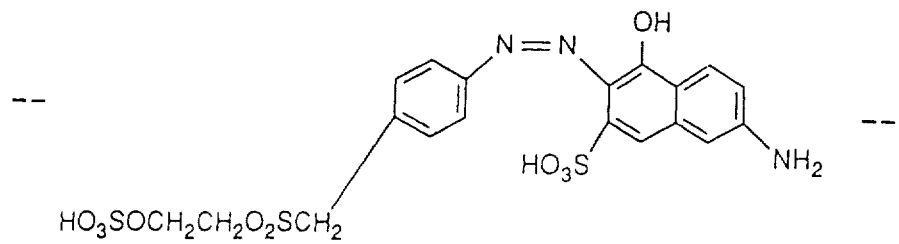 --

Col. 110, No. 143  Under " Azo component " delete

" 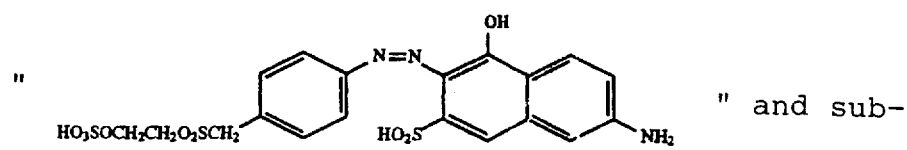 " and substitute -- 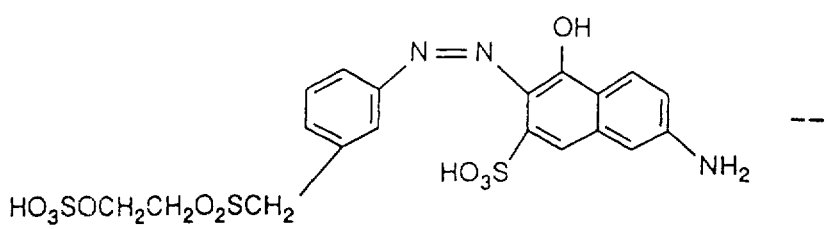 --

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

It is certified that error appears in the above-identified patent and that said Letters Patent is hereby corrected as shown below:

Col. 111, No. 147   Under " Component of the formula (V) " delete "  " and substitute -- 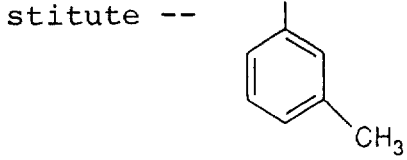 --

Col. 111, No. 148   Under " Component of the formula (V) " delete " 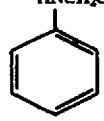 " and substitute -- 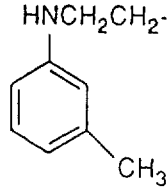 --

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

It is certified that error appears in the above-identified patent and that said Letters Patent is hereby corrected as shown below:

Col. 112, No. 149  Under " Component of the formula (V) " delete " 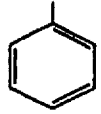 " and substitute -- 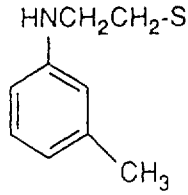 --

Col. 115, No. 153  Under " Component of the formula (V) " delete " 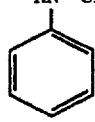 " and substitute -- 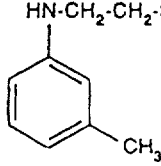 --

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

It is certified that error appears in the above-identified patent and that said Letters Patent is hereby corrected as shown below:

Col. 116, No. 154    Under " Component of the formula (V) delete " 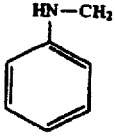 " and substitute -- 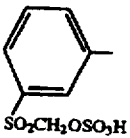 --

Col. 117, No. 156    Under " $D_1$ " delete " 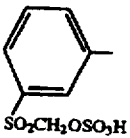 " and substitute -- 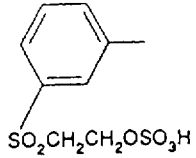 --

UNITED STATES PATENT AND TRADEMARK OFFICE
CERTIFICATE OF CORRECTION

PATENT NO. : 5,686,642
DATED : November 11, 1997
INVENTOR(S) : Bootz, et al.

It is certified that error appears in the above-identified patent and that said Letters Patent is hereby corrected as shown below:

Col. 119, line 12   After " salt " insert -- thereof --

Signed and Sealed this

Twenty-fifth Day of May, 1999

Attest:

Attesting Officer

Q. TODD DICKINSON

Acting Commissioner of Patents and Trademarks